US011998681B2

(12) United States Patent
Wensley et al.

(10) Patent No.: US 11,998,681 B2
(45) Date of Patent: Jun. 4, 2024

(54) AEROSOL DELIVERY DEVICES AND METHODS OF USING SAME

(71) Applicant: Airja, Inc., Campbell, CA (US)

(72) Inventors: Martin Wensley, San Francisco, CA (US); Richard M. Brenner, San Diego, CA (US); Beverly Connelly, Santa Cruz, CA (US)

(73) Assignee: Airja, Inc., San Francisco, CA (US)

( * ) Notice: Subject to any disclaimer, the term of this patent is extended or adjusted under 35 U.S.C. 154(b) by 13 days.

(21) Appl. No.: 17/746,785

(22) Filed: May 17, 2022

(65) Prior Publication Data

US 2022/0280731 A1  Sep. 8, 2022

Related U.S. Application Data

(63) Continuation-in-part of application No. 17/564,085, filed on Dec. 28, 2021, which is a continuation of application No. PCT/US2020/040765, filed on Jul. 2, 2020.

(60) Provisional application No. 62/870,612, filed on Jul. 3, 2019.

(51) Int. Cl.
*A61M 11/04* (2006.01)
*A61M 15/00* (2006.01)

(52) U.S. Cl.
CPC ........ *A61M 11/042* (2014.02); *A61M 15/009* (2013.01); *A61M 2205/3653* (2013.01)

(58) Field of Classification Search
CPC .......... A61M 15/0006; A61M 15/0008; A61M 11/042; A24F 40/10; A24F 40/42; A24F 40/48
See application file for complete search history.

(56) References Cited

U.S. PATENT DOCUMENTS

| | | | |
|---|---|---|---|
| 3,719,795 A | 3/1973 | Bolomier et al. | |
| 4,301,093 A | 11/1981 | Eck | |
| 5,522,385 A | 6/1996 | Lloyd et al. | |
| 2002/0189612 A1 | 12/2002 | Rand | |
| 2006/0196518 A1 | 9/2006 | Hon | |
| 2008/0223953 A1 | 9/2008 | Tomono et al. | |
| 2009/0267242 A1 | 10/2009 | Nichols et al. | |
| 2013/0160765 A1* | 6/2013 | Liu | A24F 40/46 128/202.21 |
| 2013/0199528 A1 | 8/2013 | Goodman et al. | |

(Continued)

FOREIGN PATENT DOCUMENTS

| | | |
|---|---|---|
| EP | 0957959 A2 | 11/1999 |
| EP | 3143882 A2 | 3/2017 |

(Continued)

OTHER PUBLICATIONS

EP20835237.7 Extended European Search Report dated Jun. 27, 2023.

(Continued)

*Primary Examiner* — Valerie L Woodward
(74) *Attorney, Agent, or Firm* — CP LAW GROUP PC; Cy Bates

(57) ABSTRACT

Provided herein are aerosolizing devices for substance delivery to a user. The devices have a rotational pump that receive, transport, and deliver in vapor form, a formulation having a target substance that is designed to effect a physiological change when inhaled by the user.

24 Claims, 32 Drawing Sheets

(56) References Cited

U.S. PATENT DOCUMENTS

| | | | |
|---|---|---|---|
| 2013/0220314 A1* | 8/2013 | Bottom | A61M 11/001 128/200.14 |
| 2013/0306064 A1 | 11/2013 | Thorens et al. | |
| 2014/0007863 A1 | 1/2014 | Chen | |
| 2014/0190496 A1 | 7/2014 | Wensley et al. | |
| 2014/0270730 A1* | 9/2014 | DePiano | A24F 40/70 392/394 |
| 2014/0334802 A1* | 11/2014 | Dubief | A61L 9/03 392/390 |
| 2015/0117842 A1* | 4/2015 | Brammer | A24F 40/44 392/394 |
| 2015/0335071 A1* | 11/2015 | Brinkley | H05B 1/0297 392/390 |
| 2016/0021930 A1 | 1/2016 | Minskoff et al. | |
| 2016/0309783 A1* | 10/2016 | Hopps | A61M 15/06 |
| 2017/0222526 A1 | 8/2017 | Li et al. | |
| 2018/0200458 A1 | 7/2018 | Li et al. | |
| 2019/0328040 A1 | 10/2019 | Turbi | |
| 2020/0068949 A1 | 3/2020 | Rasmussen | |
| 2021/0154418 A1 | 5/2021 | Trummer et al. | |
| 2022/0295896 A1 | 9/2022 | Connelly et al. | |

FOREIGN PATENT DOCUMENTS

| | | |
|---|---|---|
| EP | 2047880 B1 | 8/2017 |
| EP | 3993856 | 5/2022 |
| WO | WO-0021598 A1 | 4/2000 |
| WO | WO-2008042912 A2 | 4/2008 |
| WO | WO-2013022936 A1 | 2/2013 |
| WO | WO-2015112750 A1 | 7/2015 |
| WO | WO-2016118645 A1 | 7/2016 |
| WO | WO-2016155316 A1 | 10/2016 |
| WO | WO-2021003438 A1 | 1/2021 |
| WO | WO-2023225017 A1 | 11/2023 |

OTHER PUBLICATIONS

PCT/US2020/040765 International Search Report and Written Opinion dated Dec. 7, 2020.

PCT/US2023/022418 International Search Report and Written Opinion dated Aug. 23, 2023.

U.S. Appl. No. 17/564,085 Office Action dated Jul. 20, 2023.

* cited by examiner

AEROSOL DELIVERY DEVICES AND METHODS OF USING SAME

CROSS-REFERENCE

This application is a continuation-in-part of U.S. application Ser. No. 17/564,085, filed Dec. 28, 2021, which is a continuation of International Application No. PCT/US2020/040765, filed Jul. 2, 2020, which claims the benefit of U.S. Provisional Patent Application No. 62/870,612, filed Jul. 3, 2019, each of which is incorporated by reference herein in its entirety.

COPYRIGHT STATEMENT

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

BACKGROUND

The respiratory tract may be an available pathway for the rapid contacting of pharmaceutical compounds or pharmaceutical compositions with the blood stream of a subject (e.g., a patient). Drugs may be delivered to a subject via vapors or aerosols comprising pharmaceutical compounds or pharmaceutical compositions. The drugs delivered to respiratory tissues may include drugs with specific respiratory effects, or drugs that create medical responses in other tissues within a subject.

SUMMARY

Recognized herein is the need for an effective method of drug delivery via the respiratory tract utilizing a device that advantageously generates vapors or aerosols containing pharmaceutical compounds or pharmaceutical compositions. The drug delivery device of the present disclosure may be especially effective in situations where rapid pharmacokinetics are needed or gastrointestinal (GI) tract uptake issues need to be avoided. Drug delivery via the respiratory tract using provided devices may also avoid the cost and complexity of intravenous drug delivery when possible.

Some drug delivery devices may advantageously deliver particles comprising a pharmaceutical compound or pharmaceutical composition deep into the respiratory tract with a small enough particle size to permit rapid pharmacokinetics (e.g., aerosol size optimized to be in the 1-3 micrometer range Mass Median Aerodynamic Diameter (MMAD) range). A respiratory drug delivery device may also accurately meter dosages of delivered pharmaceutical compounds and minimize the degradation or decomposition of the pharmaceutical compounds.

In an aspect, the present disclosure provides a vaporizer device comprising: a reservoir configured to contain a medicament; a dispenser having an outer surface, wherein the outer surface comprises a regular array of apertures arranged thereabout, and wherein the dispenser is configured to receive the medicament pumped from the reservoir; and a heater, wherein the heater at least partially surrounds at least a portion of the dispenser, wherein the heater is configured to heat the medicament received by the dispenser.

In some embodiments, the regular array of apertures comprises a radial array of apertures. In some embodiments, the apertures in the regular array of apertures are congruent. In some embodiments, the dispenser is formed of a thermally stable material comprising metal, glass, ceramic, plastic, or any combination thereof. In some embodiments, the dispenser comprises: a first dispenser portion having a surface comprising an array of first slots; and a second dispenser portion having a surface comprising an array of second slots. In some embodiments, the array of first slots and the array of second slots interdigitate. In some embodiments, the first dispenser and the second dispenser form an open cavity therebetween. In some embodiments, the reservoir comprises a seal configured to contain the medicament within the reservoir. In some embodiments, the heater comprises a helical heater. In some embodiments, the helical heater comprises two or more helical coils. In some embodiments, the helical heater has: a diameter of about 0.006 inches to about 0.008 inches; a length of about 25 inches to about 75 inches; a working voltage of about 3 volts to about 9 volts; a working power of about 5 watts to about 50 watts; two or more helical revolutions; or any combination thereof. In some embodiments, the heater is configured to vaporize the medicament received by the dispenser. In some embodiments, the vaporizer device further comprises a housing comprising a first inlet and an outlet, wherein the housing is configured to direct a fluid from the inlet, through the heater, and to the outlet. In some embodiments, the housing further comprises a second inlet configured to isolate at most a portion of the fluid from the heater. In some embodiments, the first inlet and the second inlet, individually or in combination, have a cross sectional area of at least about 50 mm$^2$. In some embodiments, the vapor device further comprises a valve coupled to an outlet of the reservoir. In some embodiments, at least a portion of the valve is surrounded by the heater, the dispenser, or both. In some embodiments, the valve comprises a pressure release valve in a direction from the reservoir to the outlet. In some embodiments, the vaporizer device further comprises a preheater configured to heat the medicament in the reservoir, the medicament in the dispenser, or both. In some embodiments, at least a portion of the preheater is at least partially surrounded by the dispenser. In some embodiments, the vaporizer device is capable of emitting at least about 5 mg/second of the medicament. In some embodiments, the vaporizer device is capable of forming an aerosol particle of the medicament having a size of greater than about 1 µm. In some embodiments, the vaporizer device does not comprise a wick. In some embodiments, the vaporizer device further comprises an actuator configured to pump the medicament from the reservoir In another aspect, the present disclosure provides a vaporizer assembly comprising: the vaporizer device herein and a vaporizing base device comprising an actuator configured to pump the medicament from the reservoir. In some embodiments, the actuator comprises a motor, a spring, a compressed fluid container, a chemical expander, or any combination thereof.

In another aspect, the present disclosure provides an aerosolizing device for substance delivery to a user. The device may comprise a rotational pump configured to receive a formulation from a source. The formulation may comprise a target substance that is designed to effect a physiological change in the user. The rotational pump can be further configured to transport the formulation from the source and deliver the formulation in a vapor form with aid of a vaporization element for inhalation by the user.

In some embodiments, the rotational pump may comprise at least one rotatable element configured to rotate about one or more axes. The rotational pump can be configured to transport the formulation via rotational movement of the at least one rotatable element. The formulation can be flown over a surface of the rotatable element as the formulation is being transported by the rotational pump.

In some embodiments, the rotational pump may comprise an actuator configured to drive the at least one rotatable element. The actuator may comprise a magnet and/or an electromagnet. The at least one rotatable element may comprise a blade or a vane.

In some embodiments, the vaporization element may comprise a heater. The heater may comprise a resistive heating element or an induction heating element. The rotational pump can be configured to transport the formulation to the vaporization element. The vaporization element can be configured to cause the formulation to be transformed from a liquid state into the vapor form. In some embodiments, the formulation may be in a liquid state when held in the source. The formulation may be in a liquid state as it is being transported through the rotational pump.

In some embodiments, the rotational pump and the vaporization element may be provided as separate discrete components. The vaporization element may be operably coupled to the rotational pump. The vaporization element may be integrated with or on the rotational pump. The pump can be further configured to measure a viscosity of the formulation as the formulation is being transported by the pump.

In another aspect, the present disclosure provides an aerosolizing device for substance delivery to a user. The device may comprise a chamber configured to store a formulation. An internal volume of the chamber may be adjustable. The formulation may comprise a target substance that is designed to effect a physiological change in the user. The device may further comprise an actuator operably coupled to the chamber. The actuator can be configured to effect changes in the internal volume of the chamber so as to transport the formulation out of the chamber. The formulation may be delivered in a vapor form with aid of a vaporization element for inhalation by the user.

In some embodiments, the actuator may comprise a pump. The pump may be, for example, a peristaltic pump. In some embodiments, the actuator can be configured to generate a rotational motion to effect the changes in the internal volume of the chamber. In some embodiments, the actuator may comprise a plunger or piston. The actuator can be configured to generate a linear motion to effect the changes in the internal volume of the chamber.

In some embodiments, the chamber may comprise a hollow cavity for storing the formulation. The chamber may comprise a wall that is made of a flexible material. A wall of the chamber may be collapsible as the changes in the internal volume of the chamber are being affected.

In another aspect, the present disclosure provides an aerosolizing device for substance delivery to a user. The device may comprise a viscosity sensor provided in proximity to (1) a source configured to hold a formulation, wherein the formulation may comprise a target substance that is designed to effect a physiological change in the user, and/or (2) a vaporization element configured to transform the formulation to a vapor state, wherein the viscosity sensor may comprise at least one rotational element and is configured to measure a viscosity of the formulation.

In some embodiments, the device may further comprise a pump configured to transport the formulation to the vaporization element. The pump may be a rotational pump. The rotational pump can be further configured to function as the viscosity sensor. In some embodiments, the source may comprise a collapsible chamber configured to store the formulation.

In some embodiments, the device may further comprise a pump operably coupled to the chamber. The pump can be configured to effect changes in an internal volume of the chamber to transport the formulation out of the chamber. The pump can be further configured to function as the viscosity sensor. The viscosity sensor can be configured to measure the viscosity of the formulation based in part on a torque exerted on the at least one rotational element. The viscosity sensor can be configured to measure the viscosity of the formulation based in part on a response time when driving the at least one rotational element.

In some embodiments, the pump may comprise a stepped motor. The response time of the pump may be based at least in part on a measurement of a time interval that the stepped motor takes to move from one step to a next step. In some embodiments, the device may further comprise a heater configured to heat the formulation if the viscosity of the formulation is higher than a selected viscosity threshold.

In some embodiments, the device may further comprise a heater configured to modulate a temperature of the formulation to maintain the viscosity of the formulation within a selected viscosity range. The heater can be configured to modulate the temperature of the formulation substantially in real time as the formulation is being transported within the device. The heater can be configured to modulate the temperature of the formulation based at least in part on an ambient temperature in an environment in which the device is operated. The heater can be located on at least one of the pump and the source.

In some embodiments, the viscosity of the formulation is capable of being measured using the rotational pump, without using any other viscosity measurement or flowrate sensors. The viscosity of the formulation is capable of being measured using the pump, without using any other viscosity measurement or flowrate sensors.

In another aspect, the present disclosure provides an aerosolizing device for substance delivery to a user. The device may comprise: a distribution element provided adjacent to a heater. The heater can be configured to heat and transform a formulation into a vapor form. The formulation may comprise a target substance that is designed to effect a physiological change in the user. The distribution element can be configured to uniformly and consistently spread the formulation over the heater to promote the heating and transformation of the formulation into the vapor form.

In some embodiments, the distribution element may comprise an elastomeric material. The elastomeric material may be selected from the group consisting of silicone, polyisoprene, polyurethane, nitrile, natural rubber, styrene butadiene rubber, and any combination thereof. In some embodiments, the distribution element may comprise one or more channels. The formulation may be distributed over the heater along the one or more channels. The one or more channels may comprise at least one open-faced channel. In some embodiments, the distribution element may be flexible and can be configured to conform to different types and shapes of surfaces.

In some embodiments, the formulation can be uniformly and consistently spread over the heater, without being affected by an ambient environment in which the device is operated. The formulation can be uniformly and consistently spread over the heater, without being affected by a number of operations of the device and/or an age of the device. The formulation can be uniformly and consistently spread over the heater, without being affected by a viscosity of the formulation.

In some embodiments, the distribution element can be configured to be used with a plurality of formulations of different viscosities. The heating and transformation of the formulation into the vapor form can be improved using the distribution element compared to using a wick. Accordingly, the distribution element may not be subject to changes in wicking properties. In some embodiments, the distribution element does not envelope an interior surface or an outer surface of the heater.

In some embodiments, the source may comprise a collapsible reservoir or chamber.

In some embodiments, the target substance may be an active chemical or pharmaceutical ingredient. The active chemical or pharmaceutical ingredient may be selected from the group consisting of nicotine, tetrahydrocannabinol (THC), tetrahydrocannabinolic acid (THCA), cannabidiol (CBD), cannabidiolic acid (CBDA), cannabinol (CBN), cannabigerol (CBG), cannabichromene (CBC), cannabicyclol (CBL), cannabivarin (CBV), tetrahydrocannabivarin (THCV), cannabidivarin (CBDV), cannabichromevarin (CBCV), cannabigerovarin (CBGV), cannabigerol monomethyl ether (CBGM), cannabielsoin (CBE), cannabicitran (CBT), and any combinations thereof.

The formulation may be a solution, suspension, or an emulsion. In some embodiments, the formulation may comprise a carrier for holding the target substance. The carrier may comprise ethanol, propylene glycol, vegetable glycerin, water, or any combination thereof.

In some embodiments, the formulation in the vapor form may be delivered to a dispenser. The dispenser is configured to be placed in proximity to a respiratory tract of the user. The dispenser may comprise a plurality of openings permitting the formulation in the vapor form to pass through.

In some embodiments, the device may further comprise a flow channel, and the heater may be located in the flow channel. A porous layer may be provided on a surface of the heater. The porous layer may comprise a metal mesh. The porous layer may comprise glass fiber, glass frit, or ceramic frit.

In some embodiments, the device can be configured to dispense the formulation in the vapor form at a rate ranging from about 0.001 μL to about 5 μL per pump cycle. The pump can be configured to operate at a cycle frequency of less than about 50 Hz. The pump can be configured to operate at a pump rate that is dependent based in part on a rate of inhalation of the user.

In some embodiments, the formulation may further comprise a compound that is selected from the group consisting of acebutolol, acetaminophen, alprazolam, amantadine, amitriptyline, apomorphine diacetate, apomorphine hydrochloride, atropine, azatadine, betahistine, brompheniramine, bumetanide, buprenorphine, bupropion hydrochloride, butalbital, butorphanol, carbinoxamine maleate, celecoxib, chlordiazepoxide, chlorpheniramine, chlorzoxazone, ciclesonide, citalopram, clomipramine, clonazepam, clozapine, codeine, cyclobenzaprine, cyproheptadine, dapsone, diazepam, diclofenac ethyl ester, diflunisal, disopyramide, doxepin, estradiol, ephedrine, estazolam, ethacrynic acid, fenfluramine, fenoprofen, flecainide, flunitrazepam, galanthamine, granisetron, haloperidol, hydromorphone, hydroxychloroquine, ibuprofen, imipramine, indomethacin ethyl ester, indomethacin methyl ester, isocarboxazid, ketamine, ketoprofen, ketoprofen ethyl ester, ketoprofen methyl ester, ketorolac ethyl ester, ketorolac methyl ester, ketotifen, lamotrigine, lidocaine, loperamide, loratadine, loxapine, maprotiline, memantine, meperidine, metaproterenol, methoxsalen, metoprolol, mexiletine HCl, midazolam, mirtazapine, morphine, nalbuphine, naloxone, naproxen, naratriptan, nortriptyline, olanzapine, orphenadrine, oxycodone, paroxetine, pergolide, phenytoin, pindolol, piribedil, pramipexole, procainamide, prochloperazine, propafenone, propranolol, pyrilamine, quetiapine, quinidine, rizatriptan, ropinirole, sertraline, selegiline, sildenafil, spironolactone, tacrine, tadalafil, terbutaline, testosterone, thalidomide, theophylline, tocainide, toremifene, trazodone, triazolam, trifluoperazine, vaiproic acid, venlafaxine, vitamin E, zaleplon, zotepine, amoxapine, atenolol, benztropine, caffeine, doxylamine, estradiol 17-acetate, flurazepam, flurbiprofen, hydroxyzine, ibutilide, indomethacin norcholine ester, ketorolac norcholine ester, melatonin, metoclopramide, nabumetone, perphenazine, protriptyline HCl, quinine, triamterene, trimipramine, zonisamide, bergapten, chlorpromazine, colchicine, diltiazem, donepezil, eletriptan, estradiol-3,17-diacetate, efavirenz, esmolol, fentanyl, flunisolide, fluoxetine, hyoscyamine, indomethacin, isotretinoin, linezolid, meclizine, paracoxib, pioglitazone, rofecoxib, sumatriptan, tolterodine, tramadol, tranylcypromine, trimipramine maleate, valdecoxib, vardenafil, verapamil, zolmitriptan, zolpidem, zopiclone, bromazepam, buspirone, cinnarizine, dipyridamole, naltrexone, sotalol, telmisartan, temazepam, albuterol, apomorphine hydrochloride diacetate, carbinoxamine, clonidine, diphenhydramine, thambutol, fluticasone proprionate, fluconazole, lovastatin, lorazepam N,O-diacetyl, methadone, nefazodone, oxybutynin, promazine, promethazine, sibutramine, tamoxifen, tolfenamic acid, aripiprazole, astemizole, benazepril, clemastine, estradiol 17-heptanoate, fluphenazine, protriptyline, ethambutal, frovatriptan, pyrilamine maleate, scopolamine, and triamcinolene acetonide.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings (also "Figure" and "FIG." herein), of which:

DETAILED DESCRIPTION

Figure 1:
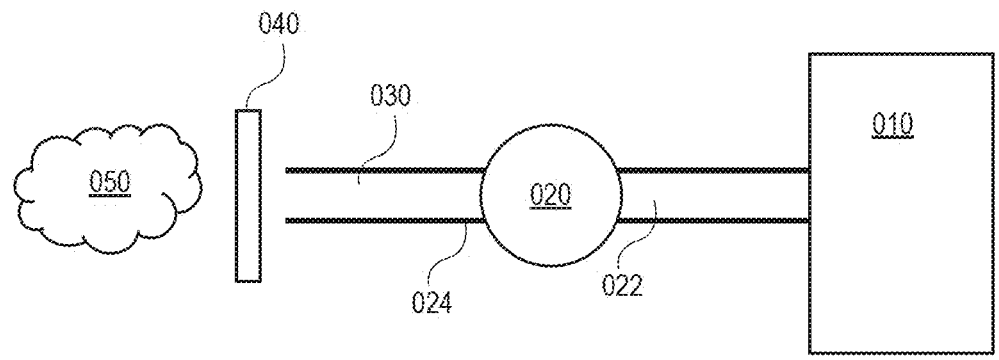
FIG. 1 depicts an example schematic of an aerosol drug delivery device.
Figure 2:
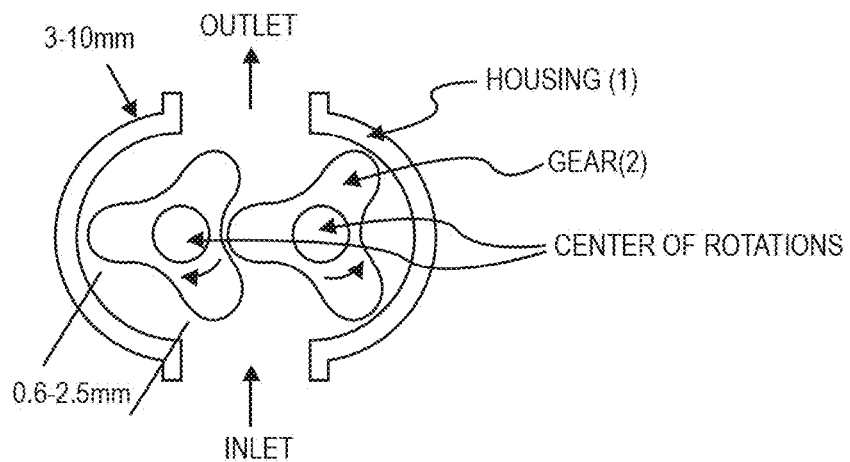
FIG. 2 illustrates an example of a geared rotary pump with three-toothed gears for pumping a liquid comprising a pharmaceutical compound or a pharmaceutical composition.

While preferable embodiments of the invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

Various terms used throughout the present description may be read and understood as follows, unless the context indicates otherwise: "or" as used throughout is inclusive, as though written "and/or"; singular articles and pronouns as used throughout include their plural forms, and vice versa; similarly, gendered pronouns include their counterpart pronouns so that pronouns should not be understood as limiting anything described herein to use, implementation, performance, etc. by a single gender; "exemplary" should be understood as "illustrative" or "exemplifying" and not necessarily as "preferred" over other embodiments. Further definitions for terms may be set out herein; these may apply to prior and subsequent instances of those terms, as will be understood from a reading of the present description.

Provided herein are aerosol drug delivery devices for effectively delivering pharmaceutical compounds to the respiratory tract. Devices of the present disclosure may be utilized for delivering any type of pharmaceutical compound, including cannabinoids, nicotine, and steroids. The aerosol drug delivery devices may offer more accurate dosing of pharmaceutical compounds and more effective control of aerosol particle size to permit more effective drug delivery further into the respiratory tract. The aerosol drug delivery devices may also minimize the degradation of delivered pharmaceuticals before and during drug delivery.

Pharmaceutical Compositions

The present disclosure provides devices for the aerosol delivery of pharmaceutical compounds and pharmaceutical compositions. A pharmaceutical compound may include any chemical species that is intended to produce a biological response in a treated subject. A pharmaceutical compound may include a small molecule drug, a peptide, a nucleic acids, or a salt. A pharmaceutical compound may comprise an active pharmaceutical ingredient (API). A pharmaceutical composition may include one or more pharmaceutical compounds. A pharmaceutical composition may comprise additional components for non-biological purposes. Additional components in a pharmaceutical composition may include cations, anions, stabilizers, antioxidants, solubilizers, viscosity enhancers, and buffers. A pharmaceutical composition may comprise one or more carrier liquids. Carrier liquids may include water, ethanol, propylene glycol, glycerin, and oils. A pharmaceutical composition may comprise a solution, mixture, or suspension. A pharmaceutical composition may comprise an emulsion. A pharmaceutical composition may comprise one or more non-volatile components.

In some instances, pharmaceutical compounds and pharmaceutical compositions of the present disclosure may be provided to a subject as a vapor or aerosol. In some instances, vapors or aerosols comprising a pharmaceutical compound or pharmaceutical composition may be generated by vaporizing or boiling of a liquid-phase component. In other instances, a vapor or aerosol may be generated by the removal of a carrier liquid followed by vaporization or the sublimation of a solid-phase pharmaceutical compound or pharmaceutical composition.

A pharmaceutical compound or pharmaceutical composition of the present disclosure may be characterized by a particular boiling temperature or sublimation point/range. A pharmaceutical compound or pharmaceutical composition may have a boiling temperature or sublimation point/range of at least about 40 degrees Celsius (° C.), 60° C., 80° C., 100° C., 120° C., 140° C., 160° C., 180° C., 200° C., 250° C., 300° C., or at least about 350° C. or more. A pharmaceutical compound or pharmaceutical composition may have a boiling temperature or sublimation point/range of no more than about 350° C., 300° C., 250° C., 200° C., 180° C., 160° C., 140° C., 120° C., 100° C., 80° C., 60° C., or no more than about 40° C. or less. A pharmaceutical compound or pharmaceutical composition may have a boiling temperature or sublimation point/range in a range from about 40° C. to about 60° C., about 40° C. to about 100° C., about 40° C. to about 200° C., about 40° C. to about 350° C., about 60° C. to about 100° C., about 60° C. to about 200° C., about 60° C. to about 350° C., about 100° C. to about 200° C., about 100° C. to about 350° C., or about 200° C. to about 350° C.

A pharmaceutical compound or composition may experience degradation during any portion of its lifecycle, including synthesis, formulation, storage, and delivery. A pharmaceutical compound or composition may experience degradation due to any mechanism, including without limitation, reduction, oxidation, isomerization, reaction, defunctionalization, precipitation, or other mechanisms of chemical loss. A pharmaceutical compound or pharmaceutical composition may be characterized by an extent of degradation at the time of delivery to a subject. An extent of degradation may be defined as the percentage, on a mass or molar basis, of pharmaceutical compound or pharmaceutical composition remaining at the time of delivery when compared to the original formulation. For example, a particular pharmaceutical compound with an original formulation concentration of about 10 mg/ml and about a 20% extent of degradation may have a concentration of about 8 mg/ml at the time of drug delivery. An extent of degradation may be measured for a specific process during drug delivery. For example, an extent of degradation may be measured during vaporization or aerosolization of a pharmaceutical compound or pharmaceutical composition to characterize the amount of degradation occurring during the process.

A pharmaceutical compound or pharmaceutical composition may have an extent of degradation of about 1%, 2%, 3%, 4%, 5%, 6%, 7%, 8%, 9%, 1, 1%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, or about 95%. A pharmaceutical compound or pharmaceutical composition may have an extent of degradation of at least about 1%, 2%, 3%, 4%, 5%, 6%, 7%, 8%, 9%, 10, 1%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or more. A pharmaceutical compound or pharmaceutical composition may have an extent of degradation of no more than about 95%, 90%, 85%, 80%, 75%, 70%, 65%, 60%, 55%, 50%, 45%, 40%, 35%, 30%, 25%, 20%, 19%, 18%, 17%, 16%, 15%, 14%, 13%, 12%, 11, 1%, 9%, 8%, 7%, 6%, 5%, 4%, 3%, 2%, 1%, or less.

An extent of degradation may be measured at a particular temperature. An extent of degradation may be measured at a temperature of at least about −40° C., −30° C., −20° C., −10° C., 0° C., 10° C., 20° C., 30° C., 40° C., 50° C., 100° C., 150° C., 200° C., 250° C., 300° C., 350° C., 400° C., or more. An extent of degradation may be measured at a temperature of no more than about 400° C., 350° C., 300° C., 250° C., 200° C., 150° C., 100° C., 50° C., 40° C., 30° C., 20° C., 10° C., 0° C., −10° C., −20° C., −30° C., −40° C., or less. An extent of degradation may be measured over a particular time period. An extent of degradation may be measured over a period of about 1 millisecond (ms), 10 ms, 100 ms, 1 second (s), 10 s, 30 s, 1 minute (min), 5 min, 10 min, 30 min, 1 hour (hr), 3 hrs, 6 hrs, 12 hrs, 1 day, 1 week, 1 month, or 1 year. An extent of degradation may be measured over a period of at least about 1 millisecond (ms), 10 ms, 100 ms, 1 second (s), 10 s, 30 s, 1 minute (min), 5 min, 10 min, 30 min, 1 hour (hr), 3 hrs, 6 hrs, 12 hrs, 1 day, 1 week, 1 month, 1 year or more. An extent of degradation may be measured over a period of no more than about 1 year, 1 month, 1 week, 1 day, 12 hrs, 6 hrs, 3 hrs, 1 hr, 30 min, 10 min, 5 min, 1 min, 30 s, 10 s, 1 s, 100 ms, 10 ms, 1 ms, or less.

A pharmaceutical composition of the present disclosure may comprise a liquid with particular rheological properties. A pharmaceutical composition may comprise a Newtonian fluid or non-Newtonian fluid. A pharmaceutical composition may be shear-thickening or shear-thinning. A pharmaceutical composition may be thixotropic, pseudoplastic, or rheopectic. A pharmaceutical composition of the present disclosure may comprise a fluid with a temperature-dependent viscosity. In some instances, increasing temperature may decrease the viscosity of a fluid comprising a pharmaceutical compound (e.g., a liquid formulation). In other instances, increasing temperature may increase the viscosity of a fluid comprising a pharmaceutical compound (e.g., a vapor formulation). A liquid formulation of a pharmaceutical composition may have a viscosity of about 1 centipoise (cP), 10 cP, 100 cP, 1000 cP, 10000 cP, 100000 cP, or 1000000 cP at a given temperature. A liquid formulation of a pharmaceutical composition may have a viscosity of at least about 1 centipoise (cP), 10 cP, 100 cP, 1000 cP, 10000 cP, 100000 cP, or 1000000 cP or more at a given temperature. A liquid formulation of a pharmaceutical composition may have a viscosity of no more than 1000000 cP, 100000 cP, 10000 cP, 1000 cP, 100 cP, 10 cP, or about 1 cP or less at a given temperature.

A pharmaceutical compound or pharmaceutical composition of the present disclosure may be selected for any purpose that is disposed to aerosol or vapor delivery to the respiratory tract. In some instances, a pharmaceutical compound or pharmaceutical composition may be selected for aerosol or vapor delivery due to the need for rapid pharmacokinetic uptake of the compound or composition. In other instances, a pharmaceutical compound or pharmaceutical composition may be selected for aerosol or vapor delivery due to the need to avoid uptake issues in the gastrointestinal tract (e.g., acid reactivity) or to avoid the cost and intrusiveness of intravenous drug delivery.

A pharmaceutical compound or pharmaceutical composition of the present disclosure may be selected from any class of pharmaceuticals that is disposed to aerosol or vapor delivery to the respiratory tract. A pharmaceutical compound or pharmaceutical composition may include, but is not limited to, an antacid, reflux suppressant, antidopaminergic, cytoprotectant, antispasmodic, opioid, cannabinoid, alpha blocker, beta blocker, calcium channel blocker, diuretic, antiarrhythmic, nitrate, antianginal, vasoconstrictor, vasodilator, antihypertensive, coagulant, anti-coagulant, haemostatic, statin, hypolipidaemic, anti-depressant, anti-psychotic, stimulant, depressant, anti-anxiety, anti-inflammatory, anesthetic, muscle relaxant, anticholinesterase, antibiotic, antiviral, antifungal, steroid, bronchodilator, antitussive, mucolytic, decongestant, antitoxin, antivenom, antihistamine, anabolic, catabolic, therapeutic peptide, therapeutic nucleic acid, vitamin, mineral, cofactor, or supplement.

Specific pharmaceutical compounds of the present disclosure may include nicotine, acebutolol, acetaminophen, alprazolam, amantadine, amitriptyline, apomorphine diacetate, apomorphine hydrochloride, atropine, azatadine, betahistine, brompheniramine, bumetanide, buprenorphine, bupropion hydrochloride, butalbital, butorphanol, carbinoxamine maleate, celecoxib, chlordiazepoxide, chlorpheniramine, chlorzoxazone, ciclesonide, citalopram, clomipramine, clonazepam, clozapine, codeine, cyclobenzaprine, cyproheptadine, dapsone, diazepam, diclofenac ethyl ester, diflunisal, disopyramide, doxepin, estradiol, ephedrine, estazolam, ethacrynic acid, fenfluramine, fenoprofen, flecainide, flunitrazepam, galanthamine, granisetron, haloperidol, hydromorphone, hydroxychloroquine, ibuprofen, imipramine, indomethacin ethyl ester, indomethacin methyl ester, isocarboxazid, ketamine, ketoprofen, ketoprofen ethyl ester, ketoprofen methyl ester, ketorolac ethyl ester, ketorolac methyl ester, ketotifen, lamotrigine, lidocaine, loperamide, loratadine, loxapine, maprotiline, memantine, meperidine, metaproterenol, methoxsalen, metoprolol, mexiletine HCl, midazolam, mirtazapine, morphine, nalbuphine, naloxone, naproxen, naratriptan, nortriptyline, olanzapine, orphenadrine, oxycodone, paroxetine, pergolide, phenytoin, pindolol, piribedil, pramipexole, procainamide, prochloperazine, propafenone, propranolol, pyrilamine, quetiapine, quinidine, rizatriptan, ropinirole, sertraline, selegiline, sildenafil, spironolactone, tacrine, tadalafil, terbutaline, testosterone, thalidomide, theophylline, tocainide, toremifene, trazodone, triazolam, trifluoperazine, vaiproic acid, venlafaxine, vitamin E, zaleplon, zotepine, amoxapine, atenolol, benztropine, caffeine, doxylamine, estradiol 17-acetate, flurazepam, flurbiprofen, hydroxyzine, ibutilide, indomethacin norcholine ester, ketorolac norcholine ester, melatonin, metoclopramide, nabumetone, perphenazine, protriptyline HCl, quinine, triamterene, trimipramine, zonisamide, bergapten, chlorpromazine, colchicine, diltiazem, donepezil, eletriptan, estradiol-3,17-diacetate, efavirenz, esmolol, fentanyl, flunisolide, fluoxetine, hyoscyamine, indomethacin, isotretinoin, linezolid, meclizine, paracoxib, pioglitazone, rofecoxib, sumatriptan, tolterodine, tramadol, tranylcypromine, trimipramine maleate, valdecoxib, vardenafil, verapamil, zolmitriptan, zolpidem, zopiclone, bromazepam, buspirone, cinnarizine, dipyridamole, naltrexone, sotalol, telmisartan, temazepam, albuterol, apomorphine hydrochloride diacetate, carbinoxamine, clonidine, diphenhydramine, thambutol, fluticasone proprionate, fluconazole, lovastatin, lorazepam N,O-diacetyl, methadone, nefazodone, oxybutynin, promazine, promethazine, sibutramine, tamoxifen, tolfenamic acid, aripiprazole, astemizole, benazepril, clemastine, estradiol 17-heptanoate, fluphenazine, protriptyline, ethambutal, frovatriptan, pyrilamine maleate, scopolamine, and triamcinolene acetonide.

A pharmaceutical compound or pharmaceutical composition may be delivered in a particular dosage to a subject. A pharmaceutical compound or pharmaceutical composition may be delivered in an amount of at least about 1 microgram (μg), 10 μg, 50 μg, 100 μg, 250 μg, 500 μg, 750 μg, 1 milligram (mg), 5 mg, 10 mg, 50 mg, or at least about 100 mg or more. A pharmaceutical compound or pharmaceutical composition may be delivered in an amount of no more than about 100 mg, 50 mg, 10 mg, 5 mg, 1 mg, 750 µg, 500 µg, 250 µg, 100 µg, 50 µg, 10 µg, or no more than about 1 µg or less.

Pharmaceutical compositions of the present disclosure may comprise one or more cannabinoid compounds. Cannabinoids comprise a class of chemical compounds that bind to the cannabinoid receptor system of many animals, including humans. Cannabinoids may be broadly grouped into categories such as endocannabinoids that are naturally produced by animals for internal signaling, phytocannabinoids that are produced by plants, and synthetic cannabinoids that are manufactured. Cannabinoids may produce a broad range of pharmacological effects, making them an active target for pharmaceutical research. Most commercially available cannabinoids are derived from plants of the *Cannabis* genus. At least 100 cannabinoid compounds have been derived from *cannabis* plants, including such common compounds as tetrahydrocannabinol (THC), cannabinol (CBN), and cannabidiol (CBD).

Cannabinoids disclosed herein include but are not limited to cannabigerol-type (CBG), cannabigerolic acid (CBGA), cannabigerolic acid monomethylether (CBGAM), cannabigerol monomethyl ether (CBGM), cannabichromene-type (CBC), cannabichromanon (CBCN), cannabichromenic acid (CBCA), cannabichromevarin-type (CBCV), cannabichromevarinic acid (CBCVA), cannabidiol-type (CBD), tetrahydrocannabinol-type (THC), iso-tetrahydrocannabinol-type (iso-THC), cannabinol-type (CBN), cannabinolic acid (CBNA), cannabinol methylether (CBNM), cannabinol-$C_4$ (CBN-$C_4$), cannabinol-$C_2$ (CBN-$C_2$), cannabiorcol (CBN-$C_1$), cannabinodiol (CBND), cannabielsoin-type (CBE), cannabielsoic acid A (CBEA-A), cannabielsoic acid B (CBEA-B), cannabicyclol-type (CBL), cannabicyclolic acid (CBLA), cannabicyclovarin (CBLV), cannabicitran-type (CBT), cannabitriol, cannabitriolvarin (CBTV), ethoxy-cannabitiolvarin (CBTVE), cannabivarin-type (CBV), cannabinodivarin (CBVD), tetrahydrocannabivarin-type (THCV), cannabidivarin-type (CBDV), cannabigerovarin-type (CBGV), cannabigerovarinic acid (CBGVA), cannabifuran (CBF), dehydrocannabifuran (DCBF), and cannabiripsol (CBR) cannabinoids.

The cannabinoids of the subject compositions disclosed herein can comprise cannabidiol-class compounds, including but not limited to cannabidiol (CBD), cannabidiolic acid (CBDA), cannabidiol monomethylether (CBDM), cannabidiol-$C_4$ (CBD-$C_4$), cannabidivarin (CBDV), cannabidivarinic acid (CBDVA), cannabidiorcol (CBD-$C_1$), and combinations thereof. CBD can comprise delta-1-cannabidiol, delta-2-cannabidiol, delta-3-cannabidiol, delta-3,7-cannabidiol, delta-4-cannabidiol, delta-5-cannabidiol, delta-6-cannabidiol, and combinations thereof.

The compositions of the present disclosure can comprise tetrahydrocannabinol (THC) as a type of cannabinoids. THC can comprise delta-9-THC, delta-8-THC, and combinations thereof. THC can comprise delta-6a,7-tetrahydrocannabinol, delta-7-tetrahydrocannabinol, delta-8-tetrahydrocannabinol, delta-9,11-tetrahydrocannabinol, delta-9-tetrahydrocannabinol, delta-10-tetrahydrocannabinol, delta-6a,10a-tetrahydrocannabinol, and combinations thereof. Delta-9-tetrahydrocannabinol can comprise stereoisomers including (6aR,10aR)-delta-9-tetrahydrocannabinol, (6aS,10aR)-delta-9-tetrahydrocannabinol, (6aS,10aS)-delta-9-tetrahydrocannabinol, (6aR,10aS)-delta-9-tetrahydrocannabinol, and combinations thereof.

The cannabinoid compositions described herein may also contain other ingredients, including terpenes. The cannabinoid compositions of the present disclosure can comprise one or more terpene compounds, including but not limited to terpenoids such as monoterpenoids, sesquiterpenoids, diterpenoids, and triterpenoids. Terpenes can be acyclic, monocyclic, or polycyclic. Terpenes can include but are not limited to myrcene, limonene, linalool, trans-ocimene, cis-ocimene, alpha-pinene, beta-pinene, alpha-humulene (alpha-caryophyllene), beta-caryophyllene, delta-3-carene, trans-gamma-bisabolene, cis-gamma-bisabolene, trans-alpha-farnesene, cis-beta-farnesene, beta-fenchol, beta-phellandrene, guajol, alpha-gualene, alpha-eudesmol, beta-eudesmol, gamma-eudesmol, terpinolene, alpha-selinene, beta-selinene, alpha-terpineol, fenchone, camphene, cis-sabinene hydrate, alpha-trans-bergamotene, alpha-cis-bergamotene, borneol, gamma-curcumene, alpha-thujene, epi-alpha-bisabolol, ipsdienol, alpha-ylangene, beta-elemene, gamma-muurolene, alpha-cadinene, alpha-longipinene, caryophyllene oxide, and combinations thereof.

Cannabinoid compositions of the present disclosure can comprise one or more additional compounds or derivatives thereof, including but not limited to pregnenolone or other compounds that counteract THC intoxication, MSM, fulvic acid, L-Theanine, Fish Oil, and phenylethylamine (PEA).

The cannabinoid compositions of the present disclosure can comprise pregnenolone, including derivatives thereof. Pregnenolone can help protect a subject from *cannabis* intoxication, for example from THC. Pregnenolone or derivatives thereof can be formulated to be water soluble. A cannabinoid composition of the present disclosure can comprise between about 1 and 50 milligrams (mg) of pregnenolone or derivatives thereof. For example, a unit dosage of the present disclosure can comprise between about 1 and 50 milligrams (mg) of pregnenolone. Cannabinoid compositions of the present disclosure (e.g., unit dosages) can comprise about 1, 2, 3, 4, 5, 6, 7, 8, 9, 10, 15, 20, 25, 30, 35, 40, 45, or 50 mg of pregnenolone. Cannabinoid compositions of the present disclosure (e.g., unit dosages) can comprise at least about 1, 2, 3, 4, 5, 6, 7, 8, 9, 10, 15, 20, 25, 30, 35, 40, 45, or 50 mg of pregnenolone. Cannabinoid compositions of the present disclosure (e.g., unit dosages) can comprise at most about 1, 2, 3, 4, 5, 6, 7, 8, 9, 10, 15, 20, 25, 30, 35, 40, 45, or 50 mg of pregnenolone.

Aerosol Drug Delivery Devices

Provided herein are devices for delivering a gas flow carrying an aerosol or vapor comprising a pharmaceutical compound or pharmaceutical composition. A device of the present disclosure may be designed for delivering a gas flow into the respiratory tract of a subject. Gas flow may be provided to a subject via any passage or orifice that provides access to the respiratory tract. In some instances, gas flows comprising a pharmaceutical compound or pharmaceutical composition may be provided to the oral cavity, nasal passage, or another opening such as a tracheotomy.

An aerosol or vapor drug delivery device may provide a pharmaceutical compound or pharmaceutical composition via a passive or active delivery mechanism. A passive aerosol or vapor delivery mechanism may include any mechanism where gas flow is provided by the input of momentum transfer from an external source. In some instances, passive delivery mechanisms may include inhalation by a subject or manual mechanical actuation of the device by a subject or administering individual. An active aerosol or vapor delivery mechanism may include any mechanism where gas flow is generated by the input of momentum transfer from an internal source. In some instances, active delivery mechanisms may include pumps, blowers, or fans that impart gas flow. In other instances, active delivery mechanisms may include gas flow generated by propellants or other pressurized gas sources.

An aerosol or vapor drug delivery device of the present disclosure may comprise a gas flow channel, a heating element, a liquid flow channel, a pump, and a reservoir. FIG. 1 depicts an exemplary schematic of a drug delivery device as provided herein. A reservoir or source 010 may contain a fluid comprising a pharmaceutical compound or pharmaceutical composition that is supplied to a heating element 040 by a rotary or rotational pump 020 that transmits the fluid through a fluid flow channel 030. The rotary or rotational pump 020 (or any other suitable different types of pumps, such as piston pumps) may have at least one inlet 022 and at least one outlet 024, that allow connection between the fluid flow channel 030 and the pump 020. The fluid may be transmitted to the heating element 040 where it is heated to form an aerosol or vapor 050.

An aerosol or vapor drug delivery device may comprise one or more reservoirs containing pharmaceutical compounds or pharmaceutical compositions. Reservoirs may be operatively connected to a pump that delivers a liquid comprising a pharmaceutical compound or a pharmaceutical composition through at least one liquid flow channel to one or more heating elements. The heating elements may provide sufficient thermal energy to convert a liquid comprising a pharmaceutical compound or pharmaceutical composition to an aerosol or vapor. The aerosol or vapor comprising a pharmaceutical compound or pharmaceutical composition may become entrained in a gas flow in the gas flow channel that carries the aerosol or vapor to a subject for administration of the pharmaceutical compound or composition. The drug delivery device of the present disclosure may comprise additional features such as housing, sensors, microprocessors, power sources (e.g., batteries) and control devices such as buttons and switches. In some instances, the drug delivery device of the present disclosure may not comprise a wicking material between the reservoir and the heating element.

An aerosol or vapor drug delivery device of the present disclosure may have several advantageous aspects that enhance the delivery of aerosols or vapors comprising pharmaceutical compounds or pharmaceutical compositions, or improve the control of the device. An aerosol or drug delivery device may have a minimized volume of the liquid flow path (e.g., small diameter needle), thereby making the response time from changes in the pumping speed rapid for the depositing of liquid onto the heating element. A non-heated or minimally heated liquid flow channel minimizes the heating of the liquid prior to vaporization. Reduced heating before vaporization may reduce the extent of degradation of a pharmaceutical compound or pharmaceutical composition during the drug delivery process. A heating element may have a large surface area in which to vaporize material from, and to reduce the thickness of the deposited liquid on the heated surface. A thinner liquid layer may increase the vaporization rate, thereby permitting less loss of pharmaceuticals by degradation, precipitation, and other loss mechanisms. The heating element may have a surface that can be wetted by liquid, or alternatively have a material (such as a fibrous material) that can hold the liquid against heater.

Figure 47:
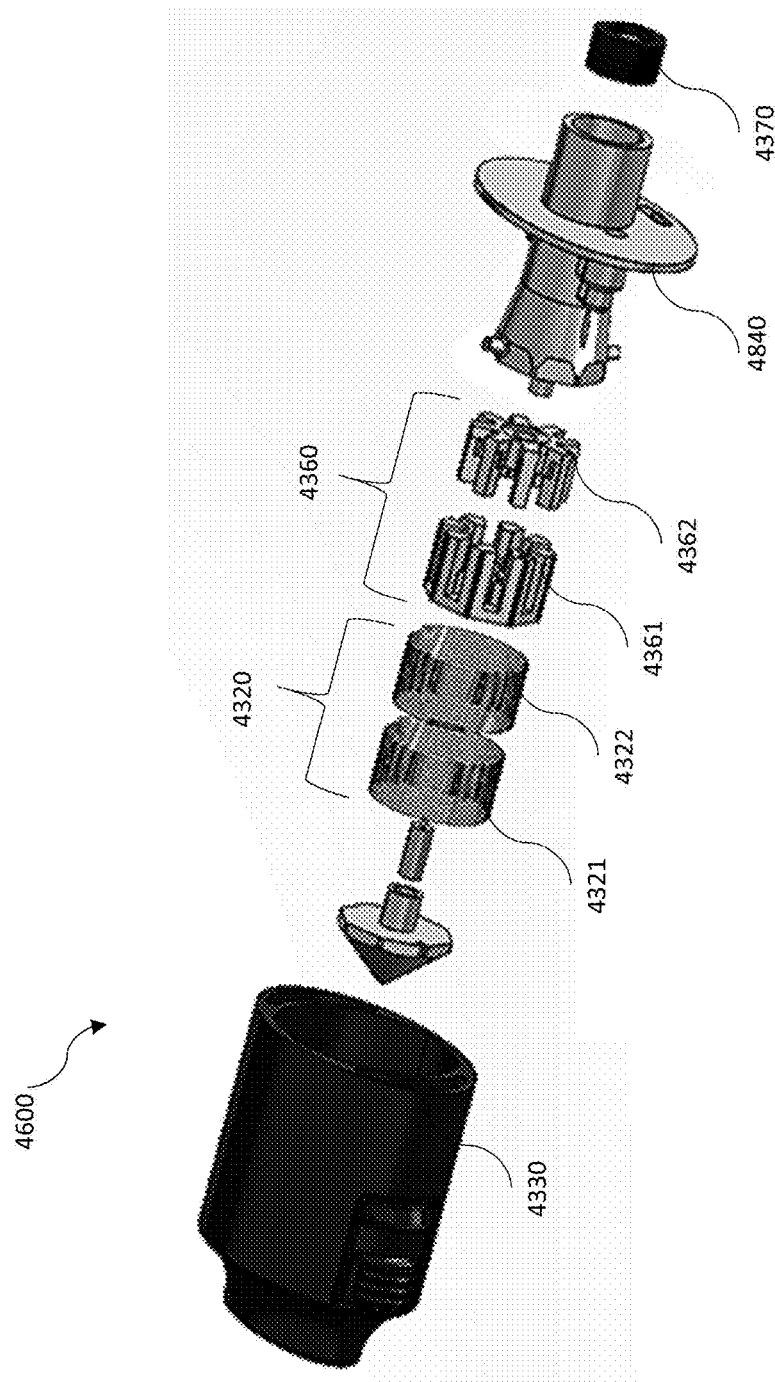
Figure 48A:
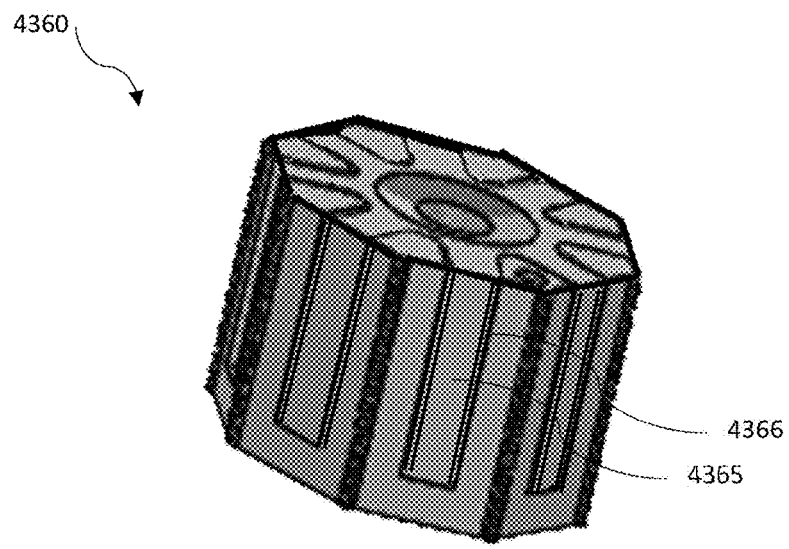
FIG. 48B shows an exploded view of an example of a ceramic dispenser.
Figure 48B:
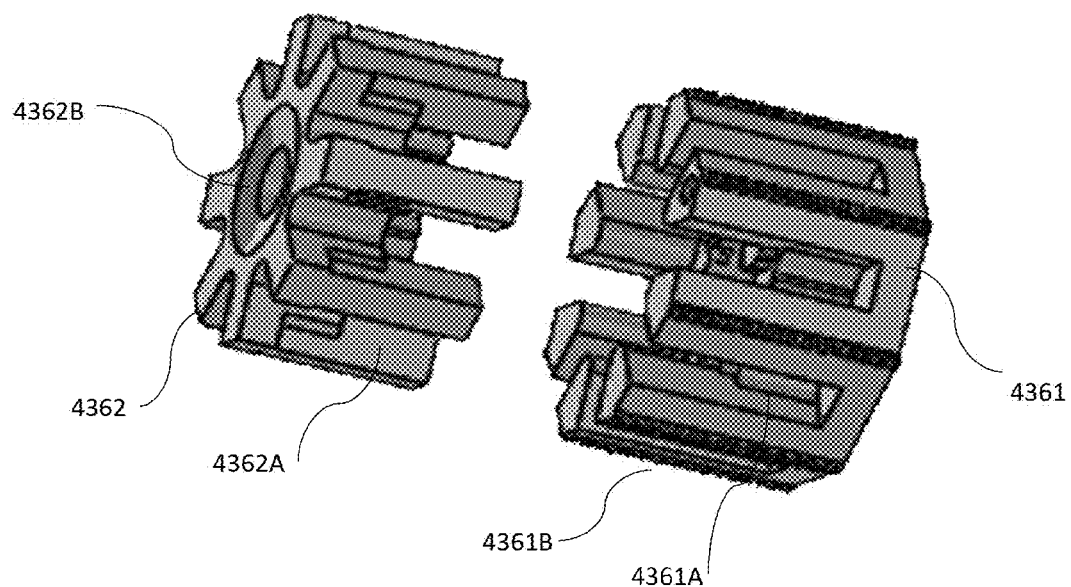

In some embodiments, the heating element may have a reasonable high and consistent temperature coefficient. The heating element may be designed to be in the 0.1 to 2.0-ohm range, or 0.4 to 1.5 ohm, allowing common resistive materials to be utilized. The heating element may be designed to minimize the air-path from the heated surface to the gas flow channel. Last, it may be advantageous to have a high temperature coefficient heating material to enable temperature measurement and control of the heater element. In some embodiments, the heating element comprises a plurality of heating coils (e.g., shaped as a single helix, a double helix, or a triple helix) (4321 and 4322) as demonstrated in FIG. 47. The heating element may comprise at least 1, 2, 3, 4, 5, 6, 7, 8, 9, 10, 20, 30, and 40 heating coils. In some embodiments, the more than one heating coils are connected to each other in parallel. Each of the heating coils may have about 0.001 to about 0.1 inches in diameter. In some embodiments, each of the heating coils may have about 0.002 to about 0.05 inches in diameter. In some embodiments, each of the heating coils may have about 0.003 to about 0.01 inches in diameter. In some embodiments, each of the heating coils may have about 0.004 to about 0.009 inches in diameter. In some embodiments, each of the heating coils may have about 0.006 to about 0.008 inches in diameter. In some embodiments, the heating coil wire may be at least about 5, 10, 15, 20, 25, 30, 35, 40, 45, 50, 55, 60, 65, 70, 75, 80, 85, 90, 95, or 100 inches in length. In some embodiments, the heating coil wire is about 50 inches in length.

In some embodiments, the aerosol generating device as disclosed herein is powered by a battery, which provides about 3 to about 7 volt range. The amount of the electrical power that may be transferred into the heating element is about from 3 to about 10 watts. When the electrical current powering the heater element is passed through a single length of the coil wire, the resultant resistance (at room temperature) may be around 4.6 ohms. Further, as the heating element increases in temperature the resistance may increase to close to 10 Ohms (due to an increase in the electrical resistance due to the temperature coefficient of nickel being relatively high. Alpha=0.006 change in Ohms/C). When the heating element comprises more than one heating coils, connected to each other in parallel, the resistance of the resultant circuit may be reduced. As a result, the power available may be increased. The total resistance $R_t$ is calculated as: $1/R_t = 1/R_1 + 1/R_2 + 1/R_3$ . . . . Since $R_1 = R_2 = R_3$ . . . this gives the expression $R_t = N/R_S$, where N is the number of parallel heater elements and $R_S$ is the resistance of a single heating coil wire.

A reservoir of the present disclosure may comprise any chamber or vessel configured to hold a liquid comprising a pharmaceutical compound or pharmaceutical composition. A reservoir may be a rigid vessel or may be flexible, deformable, or collapsible. A reservoir may comprise a polymeric or metallic material. A reservoir may comprise a flexible or collapsible material such as multi-layer laminates made of plastic and metal layers. Plastic layers can comprise one, or many layers of Polyethylene (PE), Low density PE, Linear Low Density PE, Medium Density PE, High Density PE, Polypropylene, Polyethylene Terephthalate (PET), Polyester, or Nylon. Sealant additives may include coatings that can improve performance, and can include ethylene acrylic acid, metallocene, surlyn, vinyl alcohol, or vinylidene chlorine, or metal layers deposited onto the plastic layers, or laminated between plastic layers and may be made from various aluminum alloys. A reservoir may comprise a rigid vessel with a piston or syringe type actuation member that drives fluid from the reservoir. A reservoir may comprise one or more inlets ports or outlet ports. A reservoir may comprise one or more fittings that allow the reservoir to be operatively connected to other components of the drug delivery device. A reservoir may comprise a disposable cartridge. A reservoir may compose a fixed or refillable cartridge. A reservoir may connect to one or more ports external to the housing that permit fluids including liquids and gases to be injected into the reservoir.

A reservoir may comprise a permanent or non-permanent fixture of an aerosol or drug delivery device. A permanent reservoir may comprise a fixed chamber or compartment within the aerosol or drug delivery device that can be loaded with a fluid comprising a compound for aerosol delivery. A permanent reservoir may be loaded or charged with a fluid through one or more ports. In some cases, the fluid may be charged through a port other than the port used to deliver the fluid into the device's airflow stream. A non-permanent reservoir may comprise any suitable cartridge or bladder that may accommodate a fluid for the aerosol or drug delivery device. In some cases, a reservoir may comprise a syringe or piston-plunger device. The cartridge or bladder may be a sealed or non-sealed vessel that is held or placed within the device. A seal may be made of plastic, metal foil, or any other suitable material. Non-permanent reservoirs may be intended for single use or multiple uses (e.g., refillable cartridges).

A permanent or non-permanent reservoir may be sealed to prevent fluid loss during storage or transportation, or to ensure the stability or shelf life of a compound for the aerosol or drug delivery device. A permanent or non-permanent reservoir may be sealed at a fluid delivery port with a material that can be manually or non-manually removed. The reservoir may be unsealed by a mechanism inside the aerosol or drug delivery device. A seal on a reservoir may be unsealed by a method such as mechanical rupture, thermal thinning, thermal degradation, chemical reaction, or chemical dissolution. A sealed reservoir may have an intended shelf life for the compound to be delivered. The shelf life may be a minimum, maximum, or average shelf life. A sealed reservoir may have a shelf life of about 1 day, 1 week, 1 month, 2 months, 3 months, 4 months, 5 months, 6 months, 9 months, 1 year, 1.5 years, 2 years, 3 years, 4 years, 5 years, or more than 5 years. A sealed reservoir may have a shelf life of at least about 1 day, 1 week, 1 month, 2 months, 3 months, 4 months, 5 months, 6 months, 9 months, 1 year, 1.5 years, 2 years, 3 years, 4 years, 5 years, or more than 5 years. A sealed reservoir may have a shelf life of no more than about 5 years, 4 years, 3 years, 2 years, 1.5 years, 1 year, 9 months, 6 months, 5 months, 4 months, 3 months, 2 months, 1 month, 1 week, 1 day, or less than 1 day.

A reservoir may have a total volume. A reservoir may have a volume of at least about 100 microliters (μl), 500 μl, 1 milliliter (ml), 5 ml, 10 ml, 20 ml, 30 ml, 40 ml, 50 ml, or about 100 ml. A reservoir may have a volume of at least about 100 microliters (μl), 500 μl, 1 milliliter (ml), 5 ml, 10 ml, 20 ml, 30 ml, 40 ml, 50 ml, or at least about 100 ml or more. A reservoir may have a volume of no more than about 100 ml, 50 ml, 40 ml, 30 ml, 20 ml, 10 ml, 5 ml, 1 ml, 500 μl, or no more than about 100 μl or less. A reservoir may accommodate a particular number of doses of a pharmaceutical compound or pharmaceutical composition. A reservoir may accommodate about 1, 5, 10, 20, 30, 40, 50, 60, 70, 80, 90, 100, 150, or about 200 doses of a compound or composition. A reservoir may accommodate at least about 1, 5, 10, 20, 30, 40, 50, 60, 70, 80, 90, 100, 150, or at least about 200 doses or more of a compound or composition. A reservoir may accommodate no more than about 200, 150, 100, 90, 80, 70, 60, 50, 40, 30, 20, 10, 5, or no more than about 1 dose of a compound of composition.

An aerosol or vapor drug delivery device may comprise liquid flow channels or liquid flow paths for the transfer of liquids comprising pharmaceutical compounds or pharmaceutical compositions. A flow channel or flow path may comprise materials such as polymers, metals, glass fibers, glass frits, ceramic fibers, and ceramic frits. A flow channel or flow path may comprise a high temperature polymer such as PEEK or Kapton. A flow channel or flow path may comprise one or more sections of tubing or piping. A flow channel or flow path may comprise a molded or fabricated section of housing that operatively connects two other components, e.g., a reservoir and a pump. A flow channel or flow path may comprise additional components such as fittings that secure the flow channel or path and seal the fluid flow path from leaks or contamination. A flow channel may comprise embedded or inserted components such as heaters, flow sensors, temperature sensors, and pressure sensors.

An aerosol or vapor drug delivery device may comprise one or more pumps. A pump may comprise a positive displacement pump. A pump may comprise a rotary pump. In other cases, a pump may comprise a piston pump. A pump may comprise a mechanical actuator or element that pushes or squeezes fluid from a reservoir, thereby decreasing the volume of liquid within the reservoir. A pump may be a component placed in a flow channel or flow path between a reservoir and a heating element. A pump may comprise various materials, including polymers, metals, and magnetic materials. A pump may be operatively connected to an electrical source or an electromagnetic source. A pump may be operated electrically or electromagnetically.

An aerosol or vapor drug delivery device may comprise a rotary or rotational pump. A rotary or rotational pump may comprise a housing. The pump housing may be made of plastic (e.g., injection molded plastic) or stamped metal or a combination of materials having an optimal internal volume. A rotary or rotational pump may have one or more inlets for liquid to enter the pump and one or more outlets for liquid to exit the pump. A rotary or rotational pump may comprise one or more interior members that rotate or otherwise move within the interior chamber causing liquid to be moved from the inlets to the outlets. One or more of the interior members can include a magnet, or multiple magnets, that can be used, in part, to drive the pump. A rotary or rotational pump may be configured to drive, move, or rotate one or more of the interior members. For example, the rotary or rotational pump may comprise a rotating mechanical shaft that is attached to a member or can be a moveable magnetic field that acts on a magnet, or magnets, on the interior of the pump. In some instances, the moveable magnetic field may be generated by an electromagnet.

FIGS. 2 and 3 depict a section view of a 3-toothed gear pump in which one or both of the gears may be driven. The gears may be set into a housing with at least one inlet and at least one outlet. The gears may be made of injection molded plastic such as polycarbonate, ABS, or nylon. A pump of the present disclosure may have an pump rate of about 0.1 milligrams per second (mg/s), 0.5 mg/s, 1 mg/s, 2 mg/s, 3 mg/s, 4 mg/s, 5 mg/s, 6 mg/s, 7 mg/s, 8 mg/s, 9 mg/s, or about 10 mg/s. A pump of the present disclosure may have an pump rate of about 0.1 mg/s, 0.5 mg/s, 1 mg/s, 2 mg/s, 3 mg/s, 4 mg/s, 5 mg/s, 6 mg/s, 7 mg/s, 8 mg/s, 9 mg/s, or about 10 mg/s. A pump of the present disclosure may have an inhalation rate of no more than about 10 mg/s, 9 mg/s, 8 mg/s, 7 mg/s, 6 mg/s, 5 mg/s, 4 mg/s, 3 mg/s, 2 mg/s, 1 mg/s, 0.5 mg/s, or 0.1 mg/s or less. Additionally, liquids that may be desired to be vaporized may be around unit density. This may result in desired pump rates of about 1 to 5 $mm^3$ per second.

Figure 3:
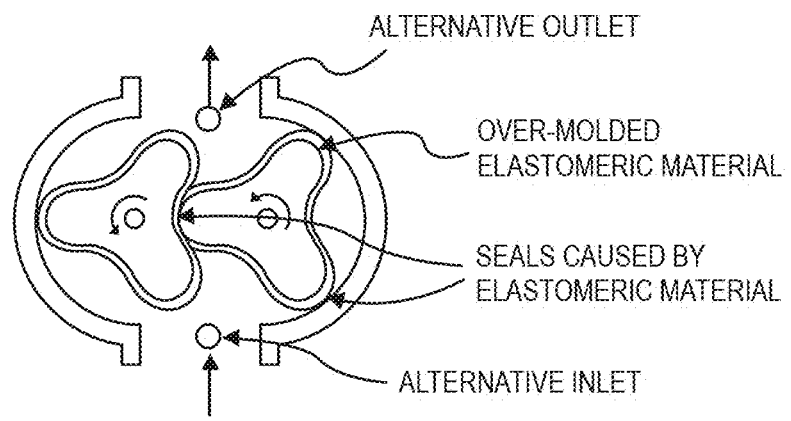
FIG. 3 illustrates another example of a geared rotary pump with three-toothed gears for pumping a liquid comprising a pharmaceutical compound or a pharmaceutical composition.
Figure 4:
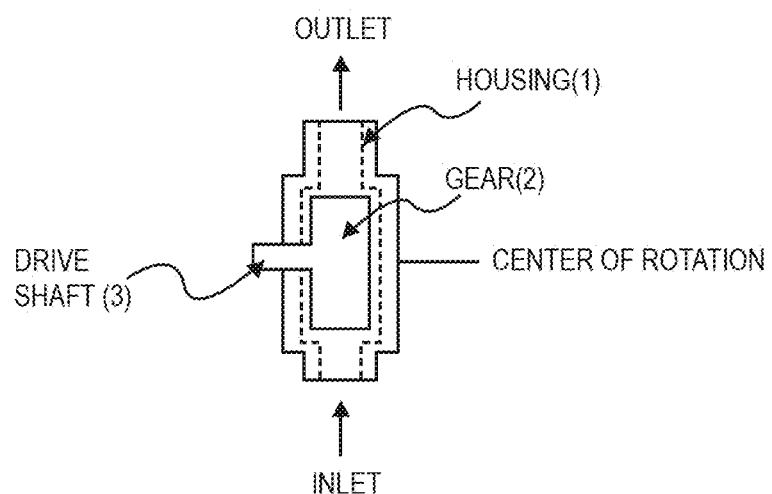
FIG. 4 depicts a side view of the rotary geared pump of FIG. 3.

In some instances, it may be desirable to have a mechanical advantage on pumping (to minimize the torque required from the drive mechanism). It may be advantageous to have a pump that rotates about once/second. A 3-toothed gear pump may have a volume of about 0.1 to about 1 $mm^3$ per tooth cavity (as there may be 2 gears). To keep the features of the pump relatively large to make manufacturing simple, the thickness of the gears may be kept to the minimum thickness that can be easily injection molded, e.g., 0.1 mm to about 0.5 mm. A cross-section area of each tooth cavity of about 0.1 to about 3.5 $mm^2$. In some instances, the tooth cavity is roughly elliptical and the depth (inside to outside) is 0.5 mm, resulting in a length of about 0.5 mm to 5.0 mm). The resultant rough size of the pump may have a diameter between be 1 and 10 mm. FIG. 3 shows a section of the same 3 toothed pump with the addition of an over-molded elastomeric material which may be added to remove tolerance issues between the gears and the housing. In this way, a more precise pump may be constructed. Additionally FIG. 3 shows another example of inlet and exit port locations for a toothed gear pump. FIG. 4 is a side view of the same pump showing the drive shaft location.

Figure 5:
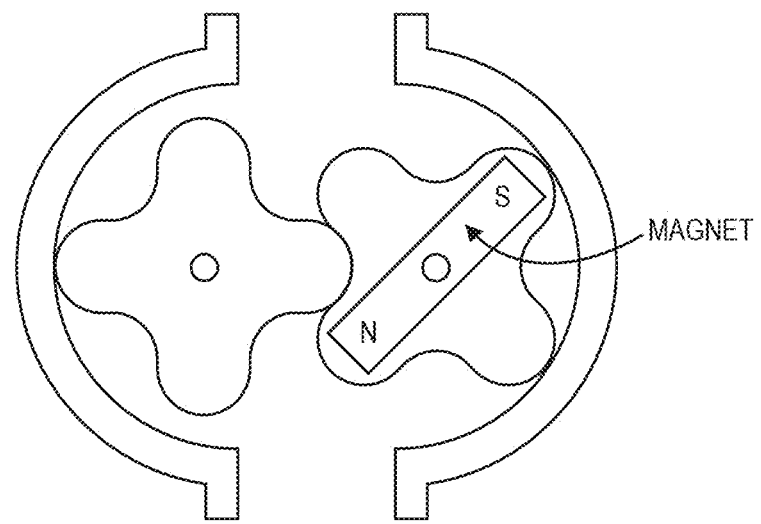
FIG. 5 shows an example schematic of a four-toothed gear pump with a gear that comprises a permanent magnet.
Figure 6:
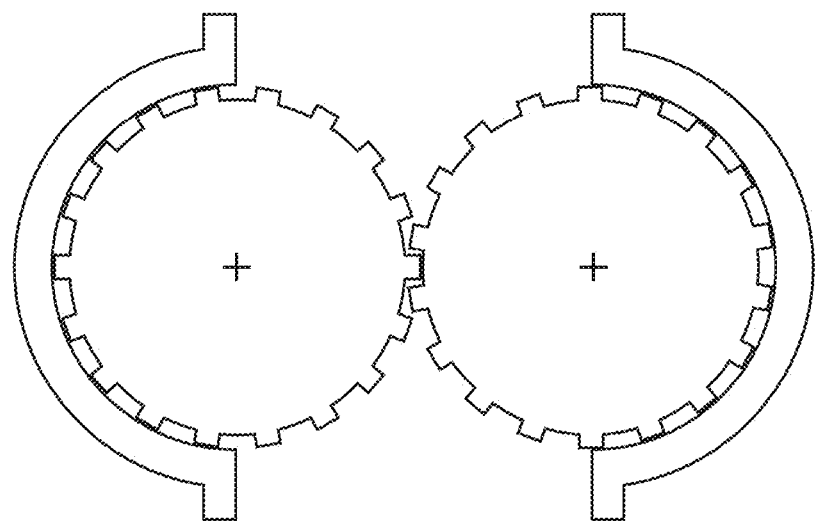
FIG. 6 depicts an example of a rotary pump that utilizes gears with smaller teeth to achieve more precise control of smaller units of fluid.

FIG. 5 is a section-view of a 4-toothed gear pump in which the interiors of one or both of the gears may comprise a permanent magnet used to drive the pump. Use of the interior magnet within the pump may drive the pump without the need for physically coupling one or more of the gears through the pump housing to a mechanical drive. A magnetic drive system may be advantageous due to minimizing leaks at mechanical coupling (e.g., where a mechanical shaft may pass through the housing) and precluding the necessity of high-tolerance part manufacture. A gear comprising a permanent magnet may be configured for any number of gear teeth. FIG. 6 shows a section of a gear pump where the number of teeth have been increased. In this manner, a smaller volume of formulation may be pumped per cycle of the pump thereby increasing the mechanical advantage of the pump drive circuit, and increasing the accuracy of the pump. If each gear has 15 teeth, then each tooth cavity may have a cross-sectional area of between about 0.01 to 0.2 $mm^2$.

Figure 7:
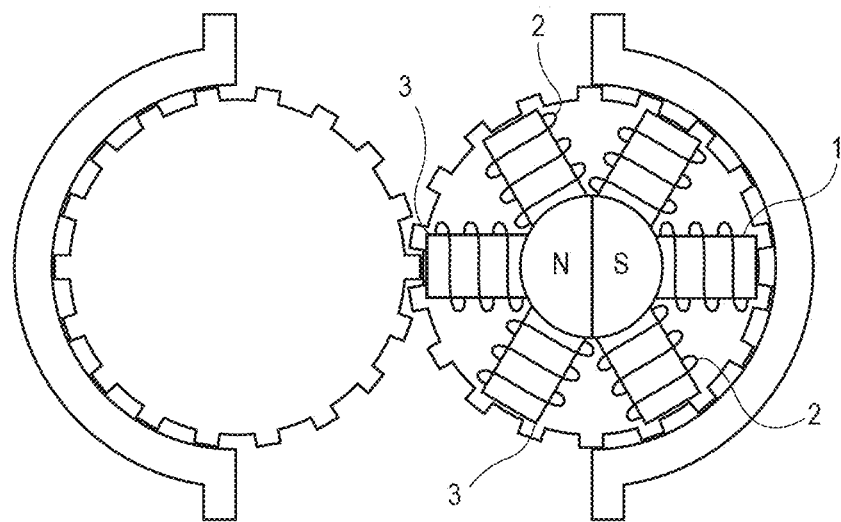
FIG. 7 illustrates an example of a rotary pump an electrically-induced magnet for controlling the pumping rate.
Figure 8:
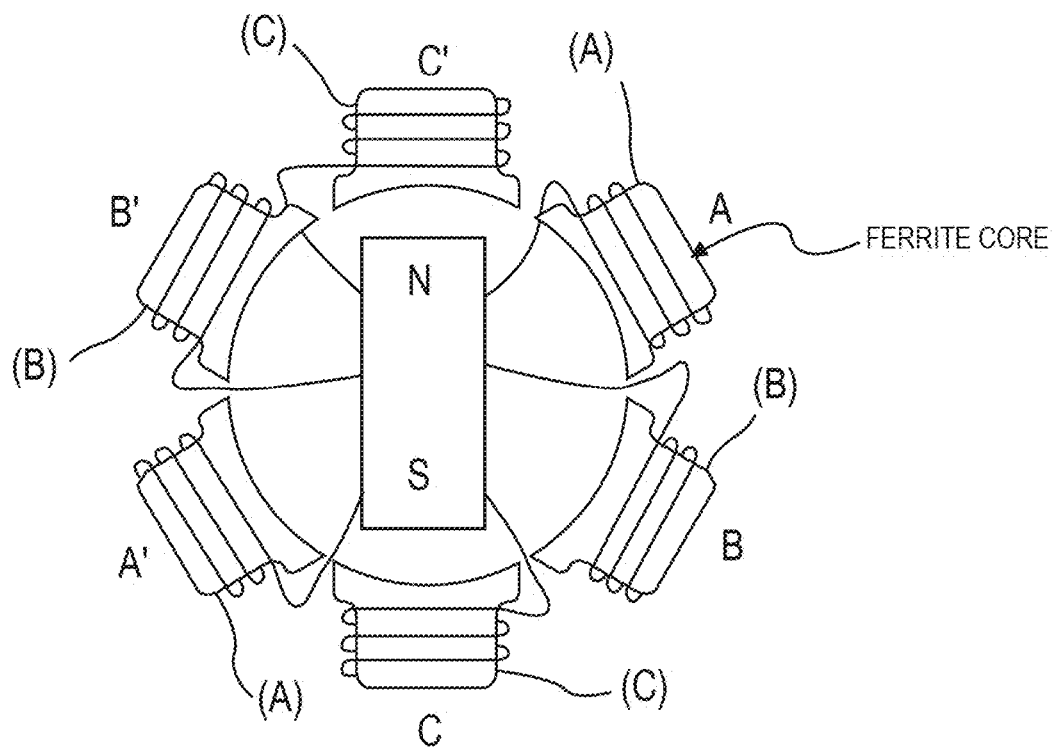
FIG. 8 depicts an example of a close-up view of a series of wound magnets for creating a variable magnetic field.

FIG. 7 shows a schematic of an exemplary magnetic drive mechanism for a gear pump. In this example 6 coils are used (3 sets of 2 coils). The coils can have an air center or the coils can be wrapped around a metaling core, or a ferrite material, can be used as the core. The 3 sets of 2 coils may be sequentially energized with a DC current in a rotational manner, causing a north and south pole magnetic field to be created, thereby driving the fixed magnet. FIG. 8 is an expanded view of the drive circuit in FIG. 7.

Figure 9:
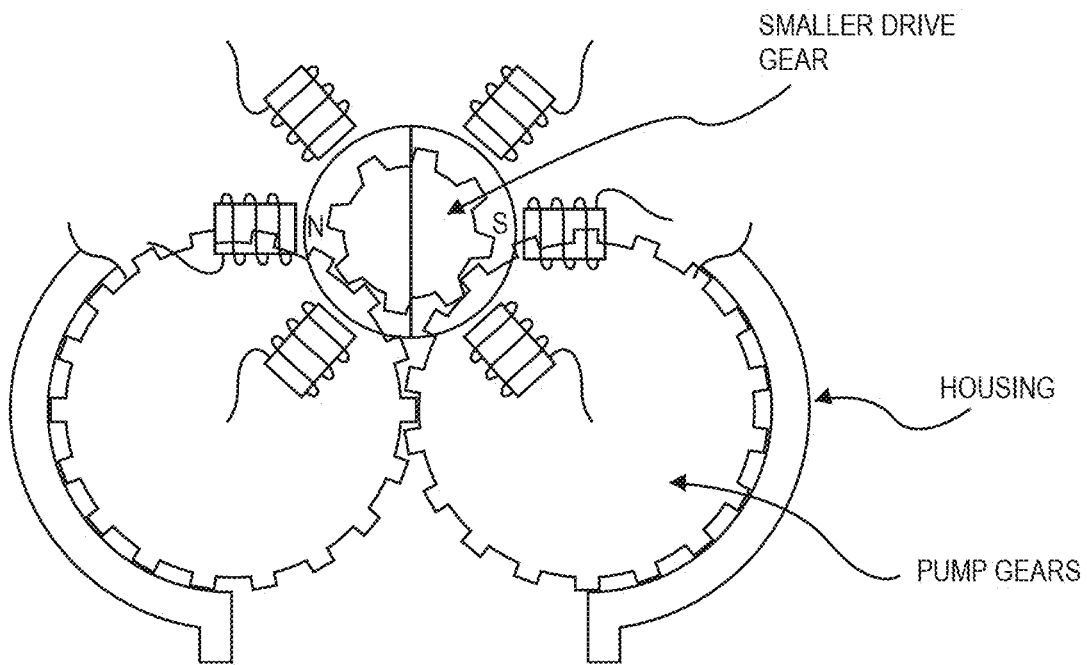
FIG. 9 shows an example of a rotary pump configuration with electromagnets disposed around a gear.
Figure 10:
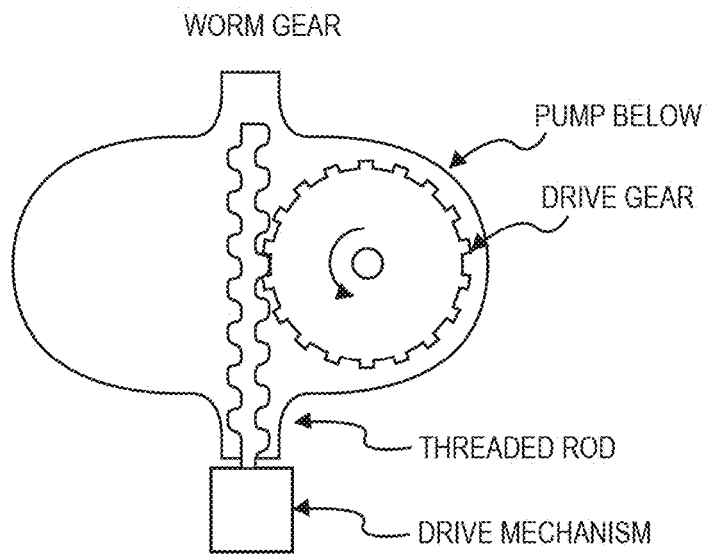
FIG. 10 shows an example of a rotary pump configuration driven by a worm gear mechanism.

FIG. 9 shows a section of a gear reduction design that may be used to increase the torque of the magnetic drive. Additionally, in this manner the amount of formulation pumped per cycle or the drive method may be reduced thereby increasing the control of the pump. As is evident additional gear reductions may be used to increase the mechanical advantage of the drive method. FIG. 10 shows a worm gear as a method to increase the mechanical gear reduction from the drive methods to the pump.

Figure 11:
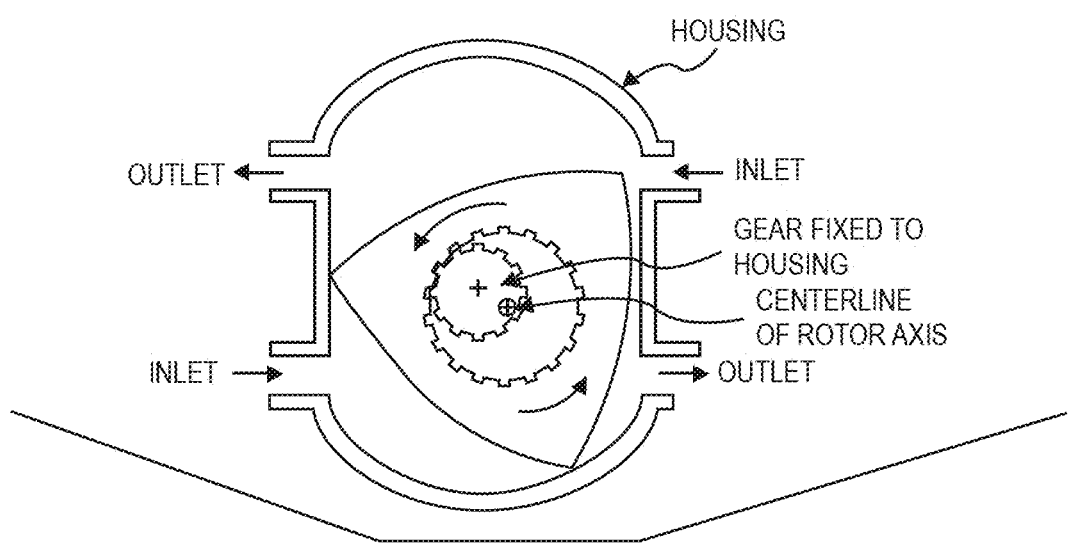
FIG. 11 illustrates an example of a rotary pump design for pushing fluid through multiple inlet and outlet ports.
Figure 12:
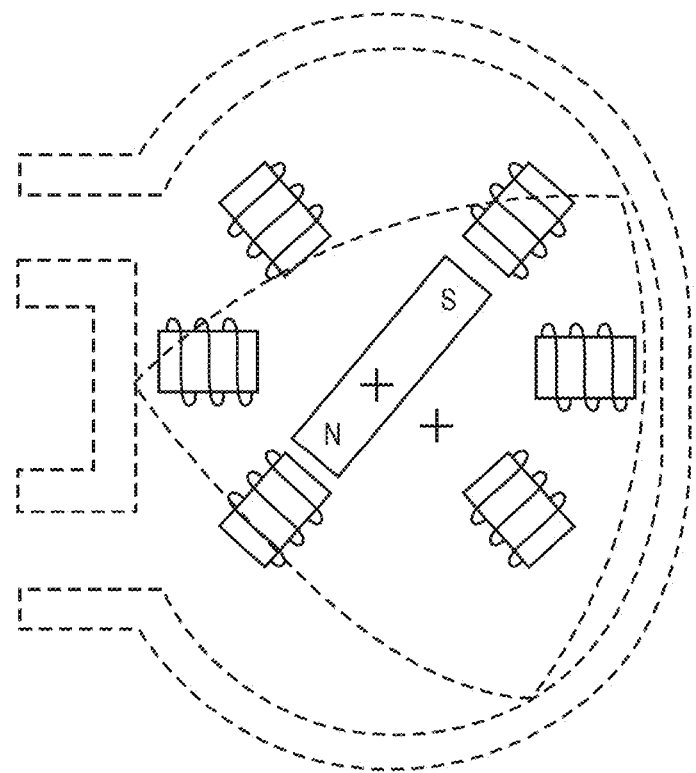
FIG. 12 depicts the rotary pump of FIG. 11 with a magnetic configuration.

FIG. 11 shows a section of an exemplary rotary pump. The smaller inner gear may be fixed to the housing and engaged with the large gear on the rotor, thereby ensuring that the rotor follows the intended path with the housing. The rotor may be driven by a shaft with an offset that rotates around the axis that may be fixed with the housing as shown and may rotate in the rotor on an axis, as also shown in FIG. 11. FIG. 12 shows the same exemplary rotary pump as FIG. 11, but with an internal magnet that may be used to drive the pump. In this example, the gears used to keep the rotor in the correct position may be located below the magnet. A similar drive method as the pump in FIG. 11 is used.

Figure 13:
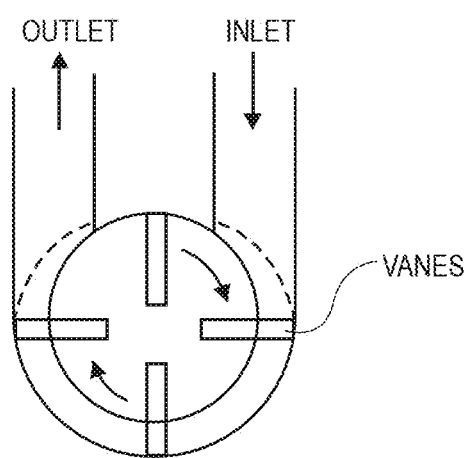
FIG. 13 shows an example of a rotary vane pump as may be utilized in a drug delivery device.

FIG. 13 shows a section of a vane pump. The vanes may be under compression against the inside wall of the housing, and as the pump rotates the vane may be free (under compression) to move, in and out, to accommodate the changes in the interior spacing of the pump. If the formulation is a liquid, (e.g., incompressible), when the vane closes off the inlet port, the section of the pump containing the liquid may have a constant cross section (the distance between the axis of rotation be consistent) until the exit port is open.

Figure 14:
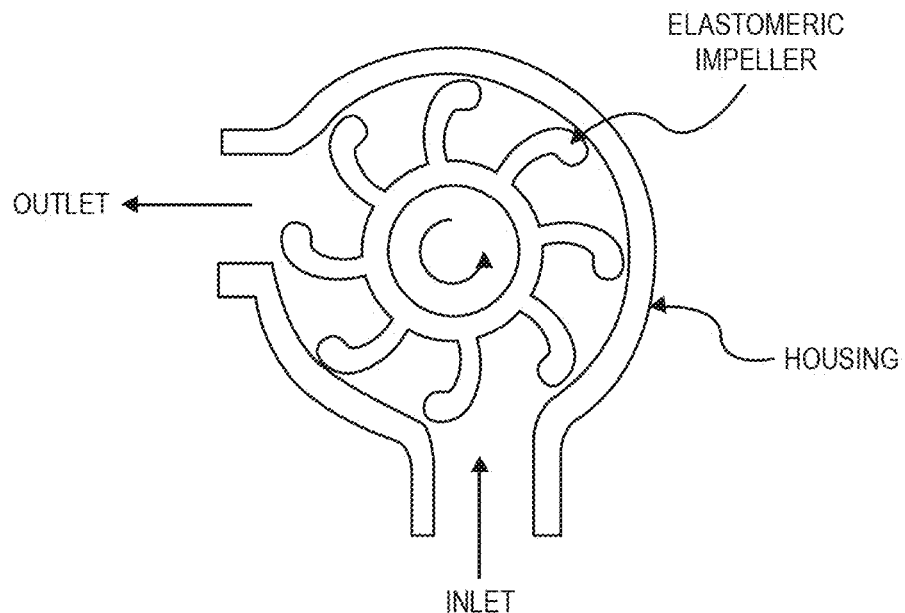
FIG. 14 depicts an example of an impeller pump that comprises a stiff elastomeric material in contact with the pump housing.

FIG. 14 shows a section of an impeller pump. The impeller materiel may be a stiff elastomeric material, or a material that is chosen to have a consistent deformation across the range of liquid viscosities of pharmaceutical compounds or pharmaceutical compositions being pumped. A pump may be designed to give a consistent pump rate regardless of the liquid composition.

An aerosol or vapor drug delivery device may comprise a method of pumping that involves driving fluid directly from the reservoir. In some instances, the drug delivery device comprises one or more rigid reservoirs with a mechanical actuator, such as a piston or syringe-like device. In other instances a drug delivery device may comprise one or more collapsible or flexible reservoirs. A collapsible or flexible reservoir may be made from a foil, or thin membrane, that forms a chamber that houses a liquid. For rigid, collapsible, or flexible reservoirs, a mechanism, component, element, or actuator is driven along the reservoir, causing the liquid housed in the reservoir to be ejected from the reservoir. The mechanism, component, element, or actuator may be mechanically or electrically coupled to a shaft for controlling the rate and volume of liquid dispensed, e.g., an electrically driven shaft that rolls two barrels along a flexible reservoir.

Figure 15:
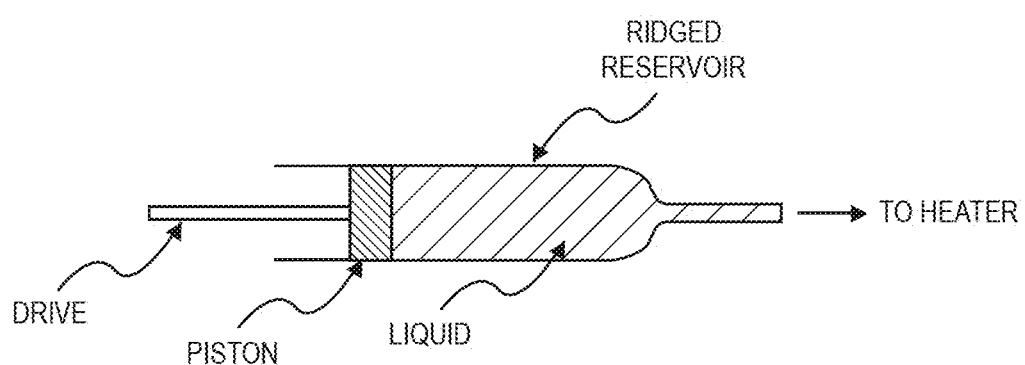
FIG. 15 illustrates an example of a piston-style pumped reservoir that drives fluid toward a heating element.

FIG. 15 shows a cross section of an exemplary linear pump and reservoir system. The reservoir may be a tube with a plunger in it (across the cross section). The plunger may be driver along the axis of the tube (similar to a syringe) to pump a liquid from the reservoir. The reservoir may be injection molded from plastic out of a material that is compatible with a liquid. If the amount of liquid to be delivered to the heating element is between about 1 mg/s and about 5 mg/s, then a cross section of the reservoir can be chosen so that a metered movement of the plunger results in the desired pump rate. For example, if the plunger is driven by a lead screw at a metered movement rate of 0.1 mm/second, then the cross-section area may need to be about 10 to about 50 $mm^2$. This may result in a diameter of the plunger (and reservoir, of about 3.5 to about 8.0 mm. In other instances, the plunger may be driven with a solenoid and pawl system in a linear manner (as compared to a rotational solenoid and pawl drive). In this instance, a reasonable lower level of the movement may be about 1.0 mm/second. This may result in a reservoir diameter of between about 1.0 and 3.0 mm.

Figure 16:
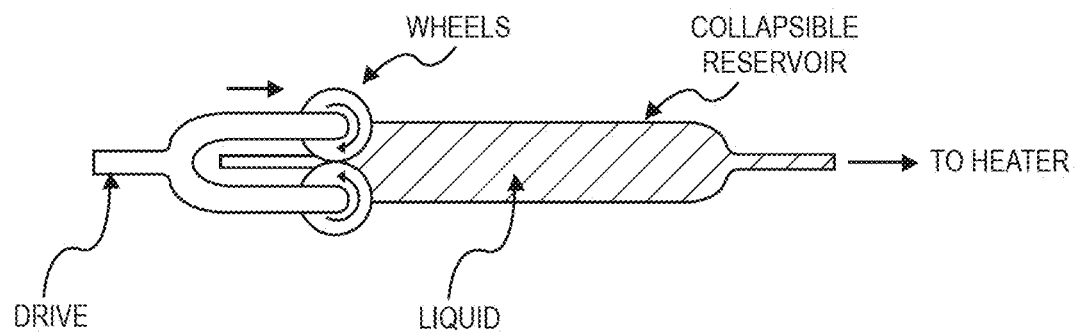
FIG. 16 shows an example of a collapsible reservoir with a wheeled pumping mechanism that drives fluid toward a heating element.
Figure 17:
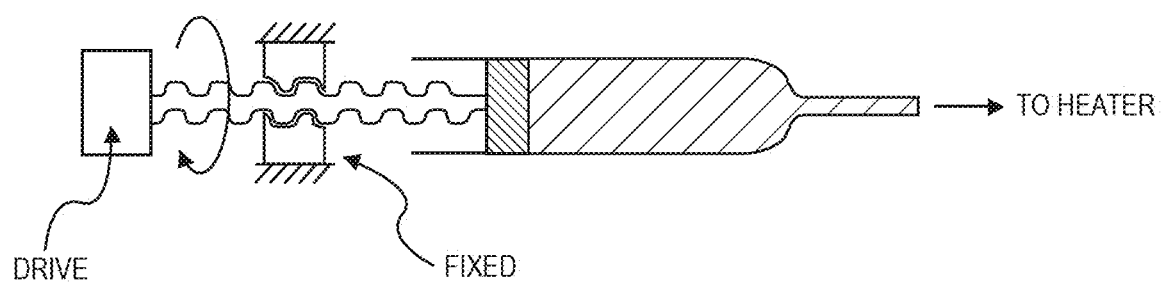
FIG. 17 depicts an example of a threaded mechanical shaft driving a piston-style reservoir that pushes fluid toward a heating element.

FIG. 16 shows a second linear pump and reservoir system which may comprise a collapsible reservoir where the liquid may be driven from the reservoir by the use of one or multiple wheels or wipes. The wheels or wipes may be moved along the reservoir to squeeze the liquid from the bag. The reservoir material may be made of a sealed multi lament material (which may include or be similar to the materials described elsewhere herein) that is commercially available. The cross section and drive mechanism sizing may be similar to what may be used on the plunger reservoir. FIG. 17 shows a screw drive system used to either push a plunger or wheels/wipes.

Figure 18:
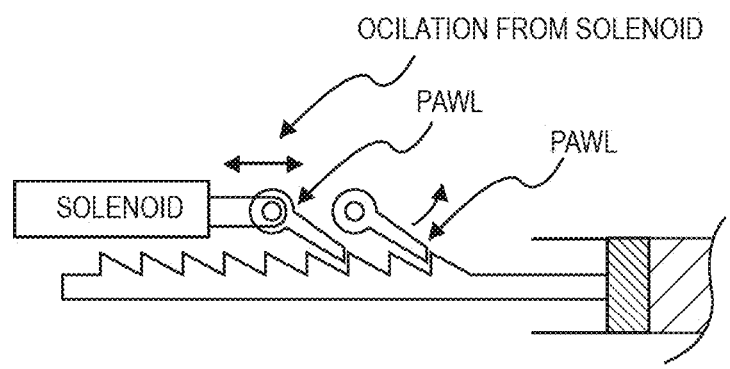
FIG. 18 illustrates an example of a solenoid and pawl style mechanism for controlling the pumping rate of a piston-style fluid reservoir.

FIG. 18 shows an exemplary linear drive that uses a solenoid and pawl system. As the solenoid is activated a pawl may push a drive member a set distance. A second pawl may fall into place, thereby precluding the member from moving backwards once the solenoid is reversed or deactivated. As the solenoid is reversed or deactivated the first pawl may slide over the teeth in the drive member to engage the next tooth.

Figure 19:
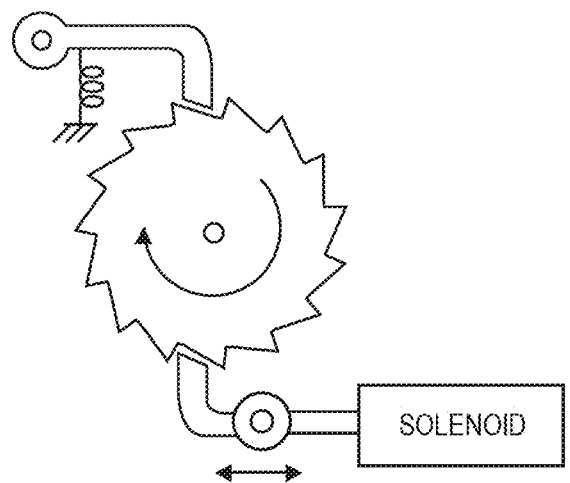
FIG. 19 depicts another example of a rotary style for utilizing a solenoid and pawls to control the pumping rate of a variable volume reservoir.

FIG. 19 shows an exemplary rotation solenoid and pawl system that may be used in conjunction with a screw drive. Similarly to the linear drive system, the solenoid may be activated such that it may drive a pawl into a rotational gear wheel and cause it to rotate. A secondary pawl may be used to preclude the wheel from turning backwards. This system may be advantageous because of the increase in the rotational drive's (over the linear drive) mechanical advantage, thereby allowing larger cross-sectional reservoirs to be employed. This rotational drive may be employed in any of the rotational pump designs such as the gear pump.

Figure 20:
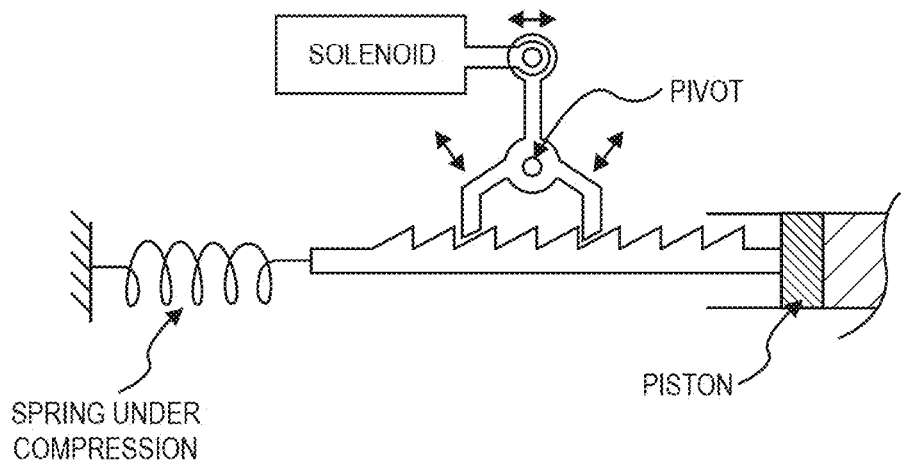
FIG. 20 demonstrates an example of the addition of a spring mechanism to a solenoid and pawl metering mechanism.

FIG. 20 shows another exemplary drive for both the plunger/syringe reservoir and the collapsible bag reservoir. In this drive, energy may be stored in a member such as a compressed spring. The energy may be then dispensed to the linear pump by releasing it in a controlled manner by use of a solenoid and pawl system. In some instances, the same mechanism can be used in a rotational manner, whereby the energy may be stored in a compressed or wound spring and the pawls may be applied to a wheel.

In some instances, the fluid properties of a liquid comprising a pharmaceutical compound or pharmaceutical composition may be altered to maintain a constant pumping rate or to allow the pump to operate. With some liquids, e.g., some of the cannabinoids, the viscosity of the liquid may be high (100,000 to as high as 1,000,000 centipoise). In such cases, liquids may require a greater amount of pumping work. The viscosity of liquids also may become higher as the temperature of the liquid drops. In some instances, the viscosity of the liquid can be measured during pumping with a rotary or rotational pump by measuring the response time of the pump to the electrical drive circuit (measurement of the time interval that the pump takes to reach the next step in the stepped motor). This may be useful with rotational pump that do not have a large mechanical reduction in the drive, such as with worm drives, or with multiple gear reductions. If an undesirable high viscosity is measured then the liquid may be heated in the pump itself, in the reservoir, in a liquid flow channel or path, or in a combination thereof, to reach a desired viscosity of the liquid. In other instances, a drug delivery device may comprise a rotational element such as an impeller that independently measures liquid viscosity somewhere within the liquid reservoir or the liquid flow path.

Figure 39A:
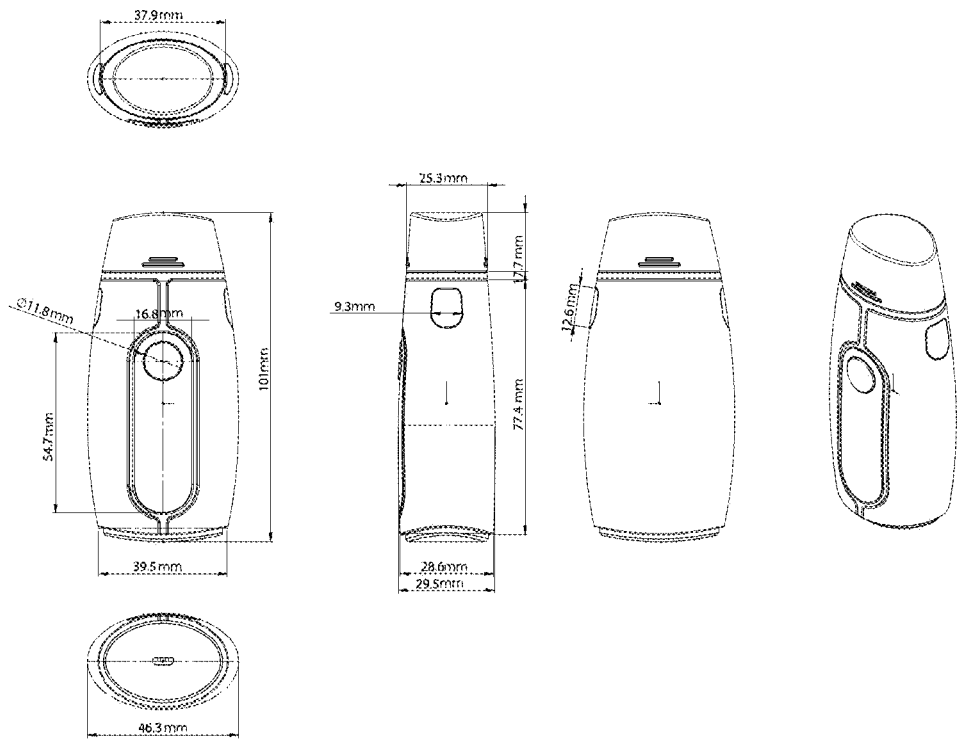
Figure 39B:
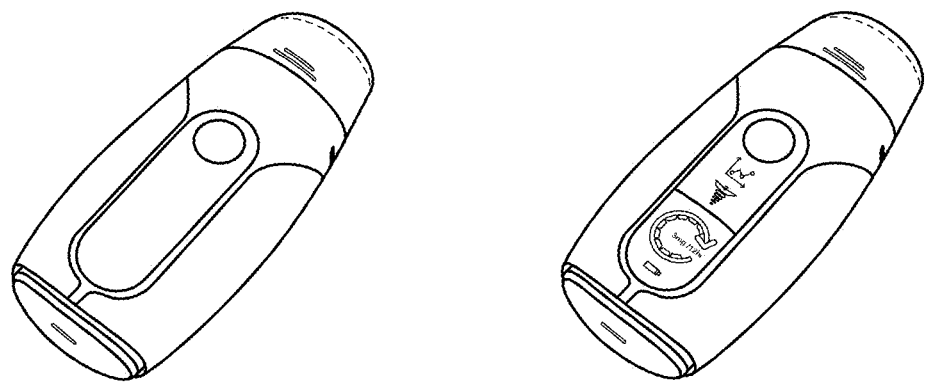

In some cases, the aerosol or vapor drug delivery device comprises a display as showed in FIGS. 39A and 39B indicating the speed of the pump, the temperature of the heating element, the viscosity of the fluid, or any combinations thereof. Further, the device as disclosed herein may comprise an actuator for adjusting the speed of the pump, the temperature of the heating element, the viscosity of the fluid, or any combinations thereof. For example, if the display shows the viscosity of the fluid is higher than intended, a user can adjust the temperature of the heating element and/or the speed of the pump until the display shows an intended viscosity of the fluid.

A rotational element for viscosity sensing may be coupled to other components necessary for sensing. A rotational element may be coupled to mechanical shafts, gears, motors wiring, power sources, circuitry components, rotational sensors, torque sensors, or microprocessors. A combination of electrical and mechanical elements including a rotational element may comprise a viscosity sensing circuit. A viscosity sensing circuit may be operatively linked to one or more heaters or heat exchanging components that alter the liquid temperature to achieve a targeted viscosity or viscosity range. A viscosity sensing circuit may have a characteristic response time. A characteristic response time may comprise the time differential between measuring a viscosity and achieving a target viscosity by altering the liquid temperature. A viscosity sensing circuit may have a characteristic response time of about 1 microsecond (μs), 10 μs, 100 μs, 500 μs, 1 millisecond (ms), 10 ms, 50 ms, 100 ms, 250 ms, 500 ms, 1 second (s), 5 s, or about 10 s. A viscosity sensing circuit may have a characteristic response time of at least about 1 microsecond (μs), 10 μs, 100 μs, 500 μs, 1 millisecond (ms), 10 ms, 50 ms, 100 ms, 250 ms, 500 ms, 1 second (s), 5 s, or about 10 s or more. A viscosity sensing circuit may have a characteristic response time of no more than about 10 s, 5 s, 1 s, 500 ms, 250 ms, 100 ms, 50 ms, 10 ms, 1 ms, 500 μs, 100 μs, 10 μs, or no more than about 1 μs or less.

An aerosol or vapor drug delivery device may comprise one or more heating elements. In some instances, a heating element may be disposed in a gas flow channel to permit aerosol or vapor formation within the inhaled or injected gas flow. In other instances, a heating element may be disposed in proximity to a fluid flow path to permit direct thermal energy input to a liquid comprising a pharmaceutical compound or pharmaceutical composition. A heating element may comprise a resistive heater or an inductive heater.

In some embodiments, a heater element may be designed without a wicking material that passively transports fluid from a reservoir. In some instances, a liquid pharmaceutical compound or pharmaceutical composition may be pumped directly onto, or into, the heater element. It may be advantageous for the design of the heater element and the liquid flow channel to be designed so that the form factor is conducive to use in conventional vaping devices, such as having the heater element aligned across the gas flow channel, or to have a size that may fit into existing "pod" type vaping cartridges.

The heater element may be made of conventional steel alloys or from other metal elements and/or alloys. Titanium, copper, or tungsten, for example, may be used if it is desirable to have a heating element with a large thermal coefficient so that the temperature of the element can be determined and controlled. This temperature control may be important for the control of temperature in conjunction with pump speed (amount of formulation vaporized). A heating element may comprise in part a polymer or elastomeric material, such as Kapton or PEEK. The polymer or elastomeric material may be resistant to thermal degradation. In some instances, the polymer or elastomeric material may be stable at a temperature of 350° C. or higher. The polymer or elastomeric material may enhance or assist the even dispersion of a liquid over the surface of the heating element or may be used to support the heater element, or electrically insulate the heater element.

A heating element may be formed from wire or may be formed from sheet (foils) of a number of metal alloys. If the heating element is to be heated by passing an electrical current though it (as compared to using electrical induction) the heating element may have an optimal electrical resistance. The electrical resistance of a heating element may be about 0.1 ohms (Ω), 0.2Ω, 0.3Ω, 0.4Ω, 0.5Ω, 0.6Ω, 0.7Ω, 0.8Ω, 0.9Ω, 1.0Ω, 1.1Ω, 1.2Ω, 1.3Ω, 1.4Ω, 1.5Ω, 1.6Ω, 1.7Ω, 1.8Ω, 1.9Ω, 2.0Ω, 2.5Ω, or about 3.0Ω. The electrical resistance of a heating element may be at least about 0.1 ohms (Q), 0.2Ω, 0.3Ω, 0.4Ω, 0.5Ω, 0.6Ω, 0.7Ω, 0.8Ω, 0.9Ω, 1.0Ω, 1.1Ω, 1.2Ω, 1.3Ω, 1.4Ω, 1.5Ω, 1.6Ω, 1.7Ω, 1.8Ω, 1.9Ω, 2.0Ω, 2.5Ω, or at least about 3.0Ω or more. The electrical resistance of a heating element may be no more than about 3.0 ohms (Q), 2.5Ω, 2.0Ω, 1.9Ω, 1.8Ω, 1.7Ω, 1.6Ω, 1.5Ω, 1.4Ω, 1.3Ω, 1.2Ω, 1.1Ω, 1.0Ω, 0.9Ω, 0.8Ω, 0.7Ω, 0.6Ω, 0.5Ω, 0.4Ω, 0.3Ω, 0.2Ω, or at least about 0.1Ω or less. The electrical resistance of heating element may be in a range from about 0.1Ω to about 0.4Ω, about 0.1Ω to about 1.0Ω, about 0.1Ω to about 1.5Ω, about 0.1Ω to about 2.0Ω, about 0.1Ω to about 3.0Ω, about 0.4Ω to about 1.0Ω, about 0.4Ω to about 1.5Ω, about 0.4Ω to about 2.0Ω, about 0.4Ω to about 3.0Ω, about 1.0Ω to about 1.5Ω, about 1.0Ω to about 2.0Ω, about 1.0Ω to about 3.0Ω, about 1.5Ω to about 2.0Ω, about 1.5Ω to about 3.0Ω, or about 2.0Ω to about 3.0Ω.

A heating element may be electrically connected to an electrical source. An electrical source may comprise one or more primary or secondary batteries. A heating element may provide a particular heat output or have a particular power requirement. A heating element may provide a heat output or power requirement of about 5 watts (W), 10 W, 15 W, 20 W, 25 W, 30 W, 35 W, 40 W, or about 50 W. A heating element may provide a heat output or power requirement of at least about 5 watts (W), 10 W, 15 W, 20 W, 25 W, 30 W, 35 W, 40 W, or at least about 50 W or more. A heating element may provide a heat output or power requirement of no more than about 50 W, 40 W, 35 W, 30 W, 25 W, 20 W, 15 W, 10 W, or about 5 W or less. In some instances, a heating element may have a heat output or power requirement of about 6 W to about 22 W.

In some instances, the heating element comprises an inductive heater. If the heating element is to be heated by way of electrical induction then an electrical coil may be positioned around the element to be heated. The coil may be in close proximity to the element and can incorporate the use of ferrite material and other materials to direct the electromagnetic field (energy) to the element. The frequency of the alternating electrical current in the inductive coil may be chosen with the geometry of the element in mind. As the thickness of the element is increased, the frequency may be lowered. For example, if the "skin" of the element is for example 0.004 in. in thickness then a frequency may be around 200-400 khz.

In some instances, a heating element of the present disclosure may be in physical contact with a fibrous or fritted material that aids in dispersing a liquid compound or composition over the surface of the heating element. In other instances, a liquid flow channel or path may comprise a material (e.g., fritted metal) that is resistively or inductively heated at the outlet of the channel or path to create an aerosol or vapor from a flowing liquid.

Figure 21:
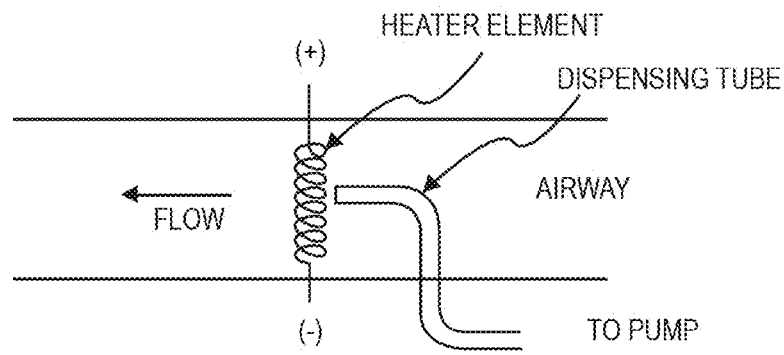
FIG. 21 depicts an example of a resistive heating element configured across a gas flow channel with a liquid flow channel positioned to dispense fluid onto the heating element.

FIG. 21 shows a heater element which may be a coil of wire in a gas flow channel. The wire may be made of a metal alloy, such as stainless steel, a nickel chrome alloy, titanium, or similar alloy. In some instances, the diameter of the wire may be in a range from about 0.1 mm to about 0.5 mm. The length may be about 1 to about 20 mm. The electrical resistance may be between 0.1 and 3 ohms. The pitch of the coil may be about 1.2 to 2.0 times the diameter of the heater wire. In some instances, a liquid flow channel may dispense a liquid onto the heating element. The tube may be made from metal, glass, ceramic, or a high temperature plastic such as PEEK or Kapton.

Figure 22:
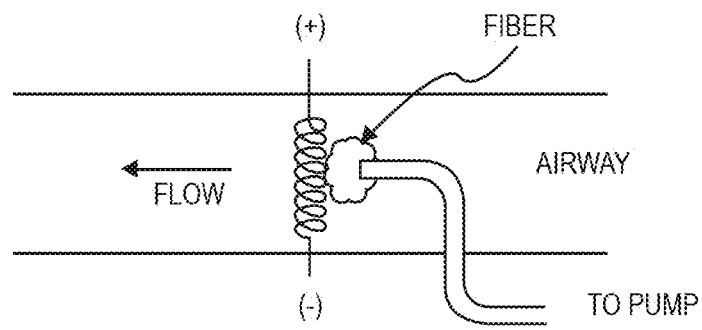
FIG. 22 shows the device of FIG. 21, with an additional fibrous material configured to spread liquid from the flow channel to the heating element.
Figure 23:
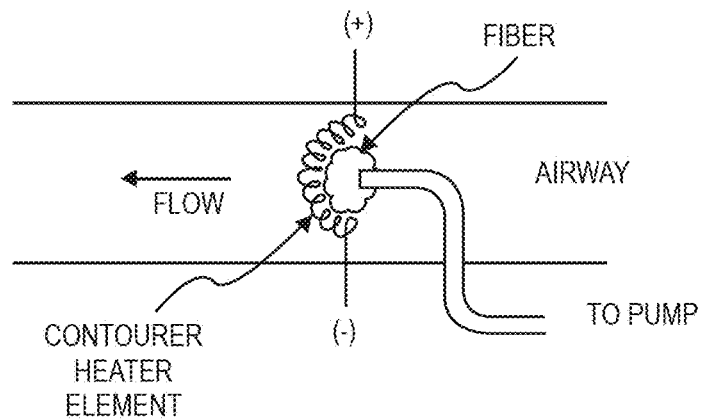
FIG. 23 demonstrates an example of a heating element contoured to the shape of a fibrous material to permit improved dispersion of the liquid onto the heating element surface.
Figure 24:
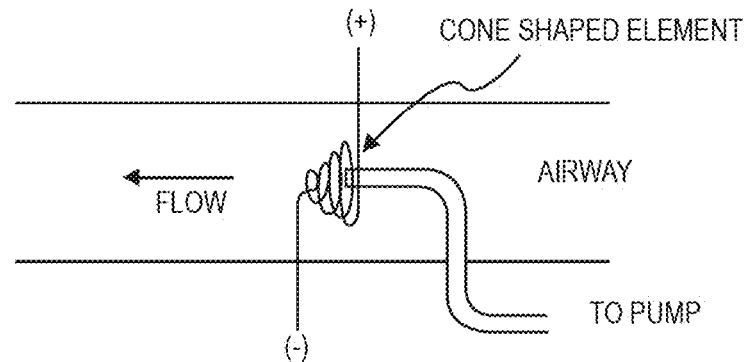
FIG. 24 shows an example of a cone shaped heating element that surround the outlet of a liquid flow channel.

FIG. 22 shows the configuration of FIG. 21 with a porous material placed at the end of the liquid flow channel that aids in dispensing the liquid onto the heating element. This porous material may be made from glass fiber, or a glass or ceramic frit. FIG. 23 is the same configuration as FIG. 22 but with the heating element wound into a space that contour around the porous material and helps to hold it in place. FIG. 24 has a heater element that is wound into an alternative shape to hold the porous material.

Figure 25:
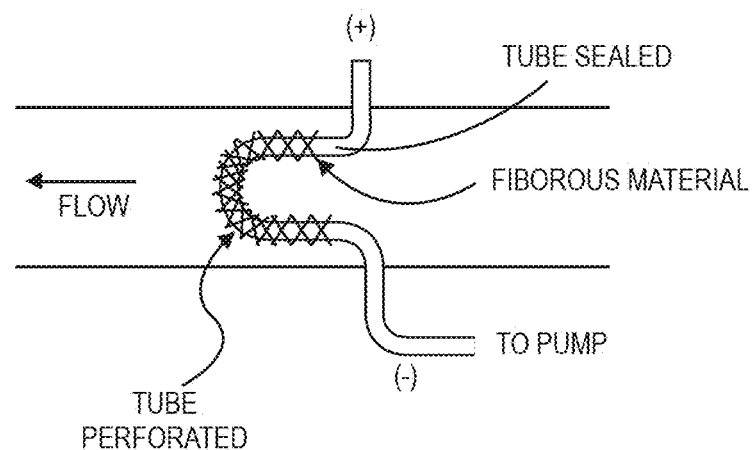
FIG. 25 illustrates an example of a heating element contacted with a liquid flow channel comprising a porous section within the gas flow channel.

FIG. 25 shows a liquid flow channel that may also be used as a heating element. In this instance, the flow channel can have on its exterior a porous material that aids in increasing the heated surface area. Examples of the porous material may include metal fibrous mats, and metal screens. Alternatively, the tube may have a surface treatment applied to the exterior that increases the surface area and increases the wetting properties. In some instances, a liquid flow channel may be surface-treated with ceramics. These ceramics may be formed on the surface of the heating element by oxidizing the surface such as with titanium into titanium oxide.

Figure 26:
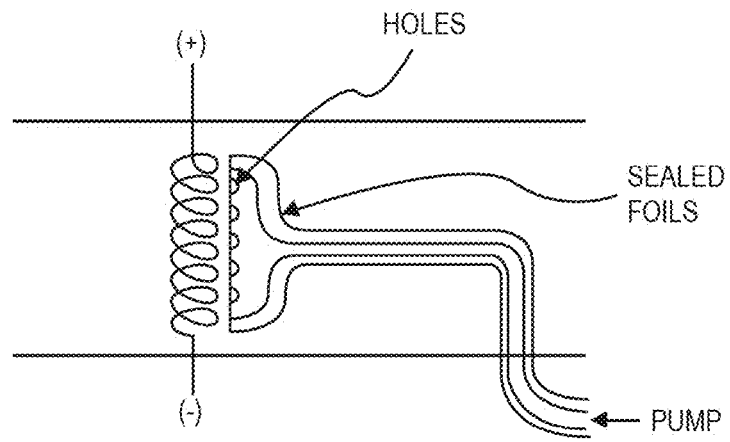
FIG. 26 depicts an example of a liquid flow channel that dispenses a liquid onto a heating element using a pierced metal foil outlet.

FIG. 26 shows a liquid flow channel that may be made of metallic foil, such as stainless steel. This foil may be folded onto itself and either welded (for example seam welded) or a seal may be formed in the fold itself. At the end of the liquid flow channel may be a series of holes that are used to spread out the liquid onto the heating element. Alternately the liquid flow channel may be made from a sheet of high temperature plastic such as PEEK or Kapton.

Figure 27:
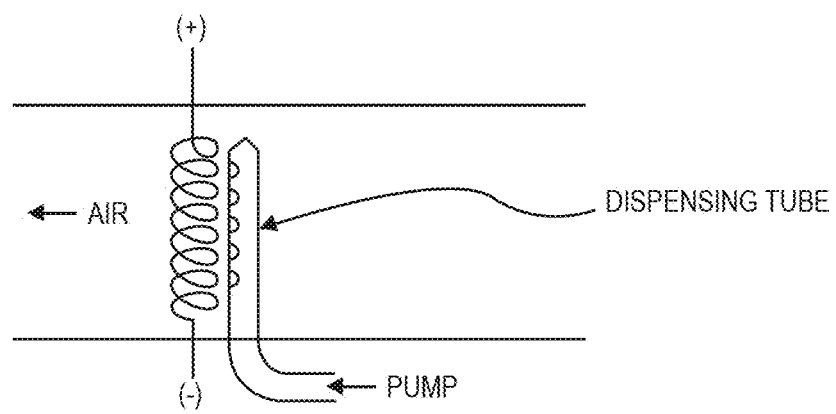
FIG. 27 shows an example of a liquid flow channel that ends with an outlet comprising a series of holes in proximity to the heating element.
Figure 28:
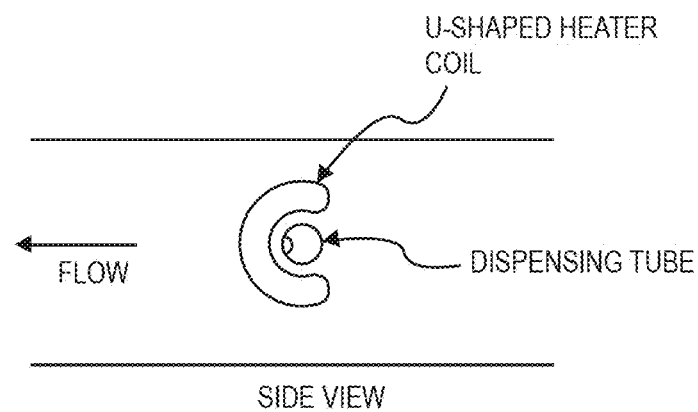
FIG. 28 depicts a side view schematic of the configuration depicted in FIG. 27 (with the heater element formed into a U shaped helix).

FIG. 27 depicts a dispenser that may be a metallic tube, or another material, with a series of holes in it that run along the helical heating element. FIG. 28 shows a configuration similar to that of FIG. 27 but one in which the heater element may be wound in a way to form a cross section that fits partially around the liquid flow channel.

Figure 29:
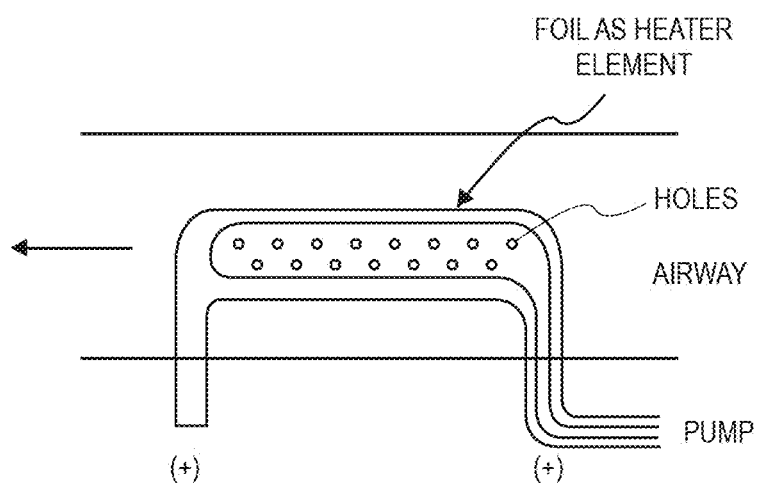
FIG. 29 illustrates an example of a foil heating element designed to vaporize a liquid as it is pushed out through holes within the foil of the heating element.
Figure 30:
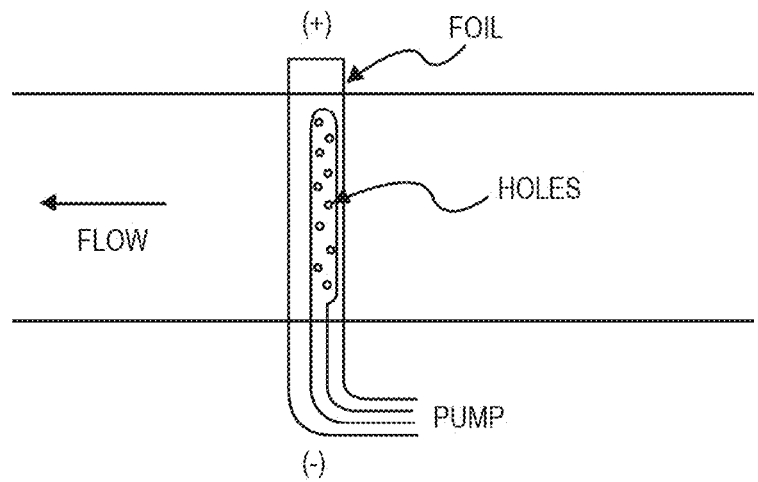
FIG. 30 depicts the heating and dispensing apparatus of FIG. 29 configured across the gas flow channel rather than along it.

FIG. 29 shows an exemplary liquid flow channel and heating element combination made from metallic foil that may be welded together to form a channel that carries the liquid. Electrical current may be passed through the foil to heat the liquid. In some instances, 12.5 micron (0.0005 in) thick stainless steel can be used. FIG. 30 shows a configuration similar to FIG. 29, but one in which the vaporization zone may be placed across the gas flow channel as compared to along the gas flow channel.

Figure 31:
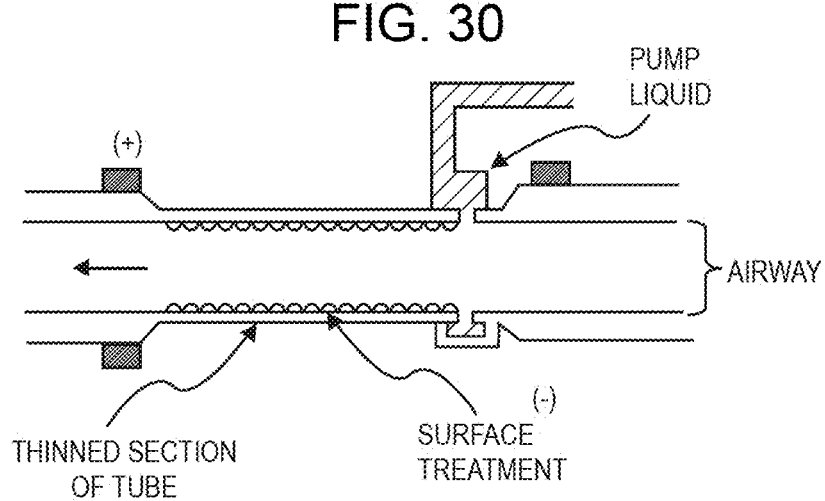
FIG. 31 shows an example of a heating element with a treated surface for improved dispersion of a liquid on the heating element surface.

FIG. 31 shows a gas flow channel made from a thinned metallic tube that also may be used as the heating element with a heated surface. Liquid may be pumped into the interior of the tube through small holes from the exterior. The tube may be heated by dissipating an electrical current within the material that comprises the tube.

Figure 32:
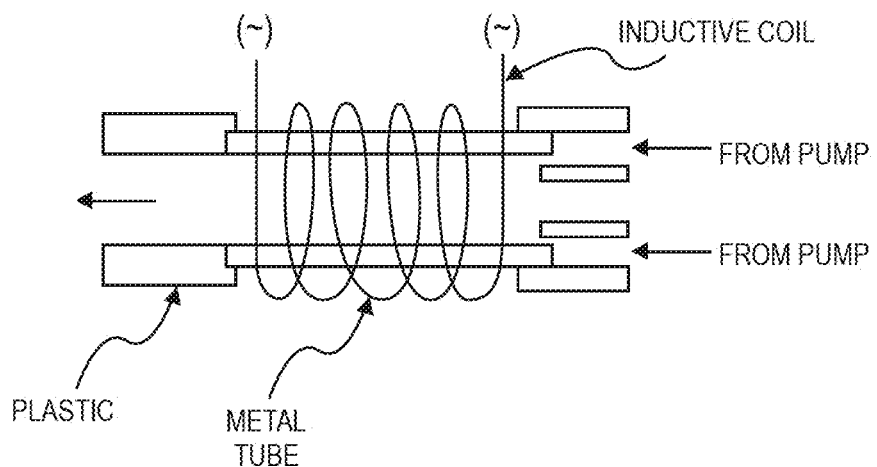
FIG. 32 illustrates an example of a configuration for an inductively-heated metal gas flow channel.

FIG. 32 shows a metal tube where liquid may be dispensed onto the interior surface. The tube may be heated using electrical induction. A coil may be positioned around the tube and an alternating electrical current may be passed through the coil. Example frequencies for inductive heating may be in a range from about 100 kHz to about 500 khz. This alternating electromagnetic field induces or causes a current in the tube, thereby heating the tube.

Figure 33:
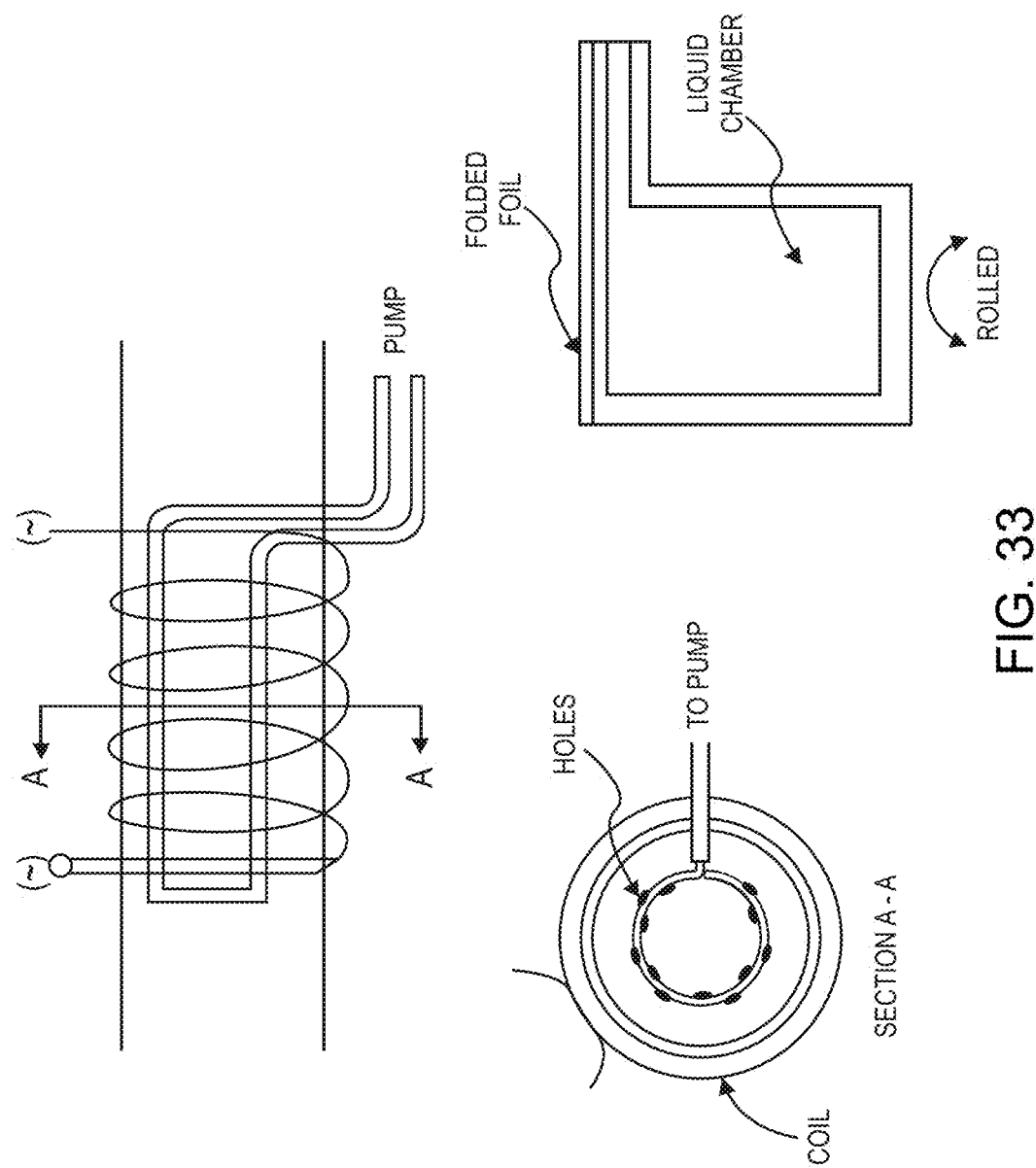
FIG. 33 depicts an example of an inductive heating configuration for the outlet of a liquid flow channel.

FIG. 33 shows an exemplary inductive heater where the heater element may be made from a folded metal foil. The fold in the foil may form a chamber where the liquid is transported to the gas flow channel. The foil tube may be held in the middle of a gas flow channel.

Figure 34:
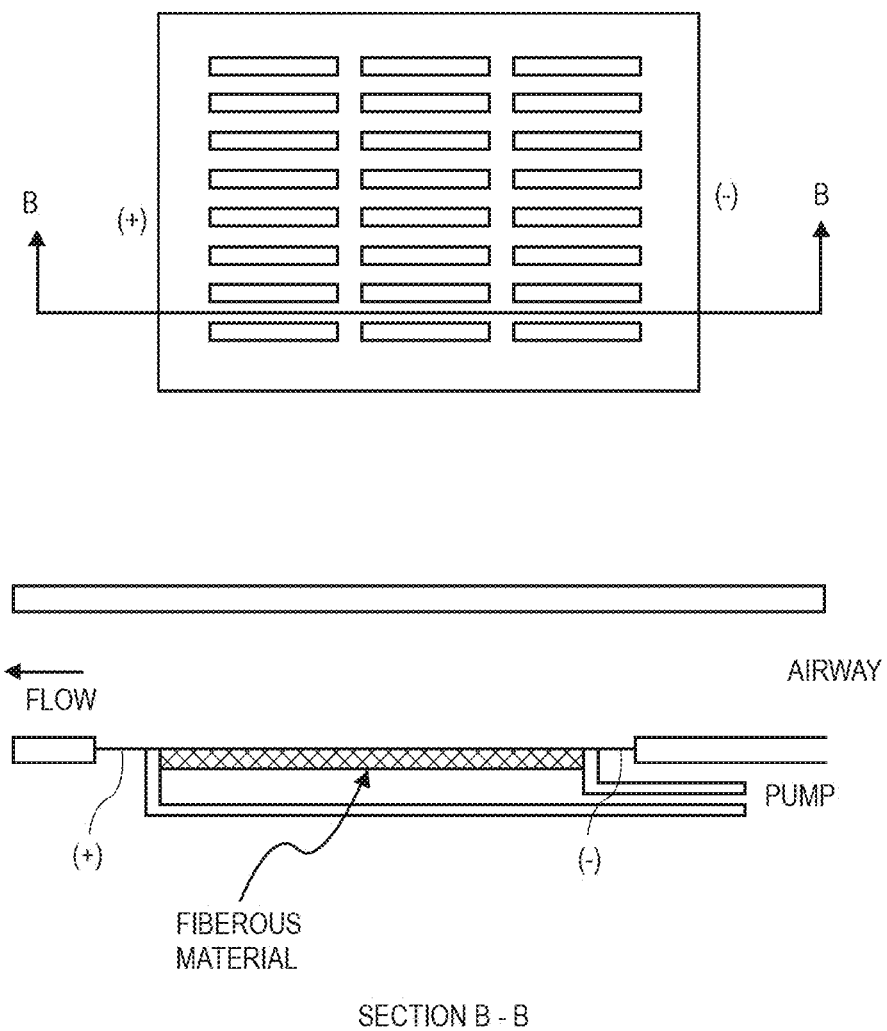
FIG. 34 illustrates an example of a heating element configured from a thin metallic foil.
Figure 35:
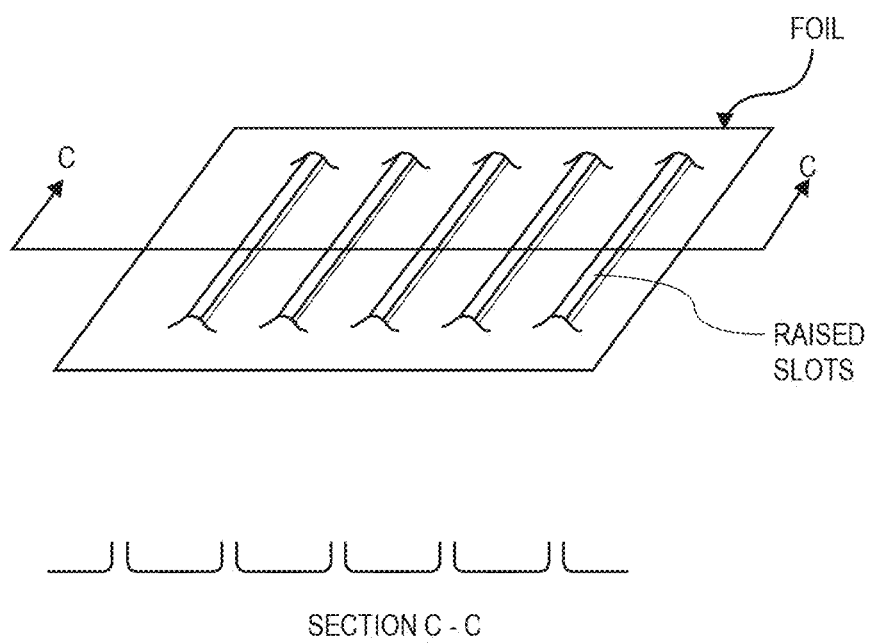
FIG. 35 shows an example of a liquid flow channel formed by punching metal foil to form a raised channel.
Figure 36:
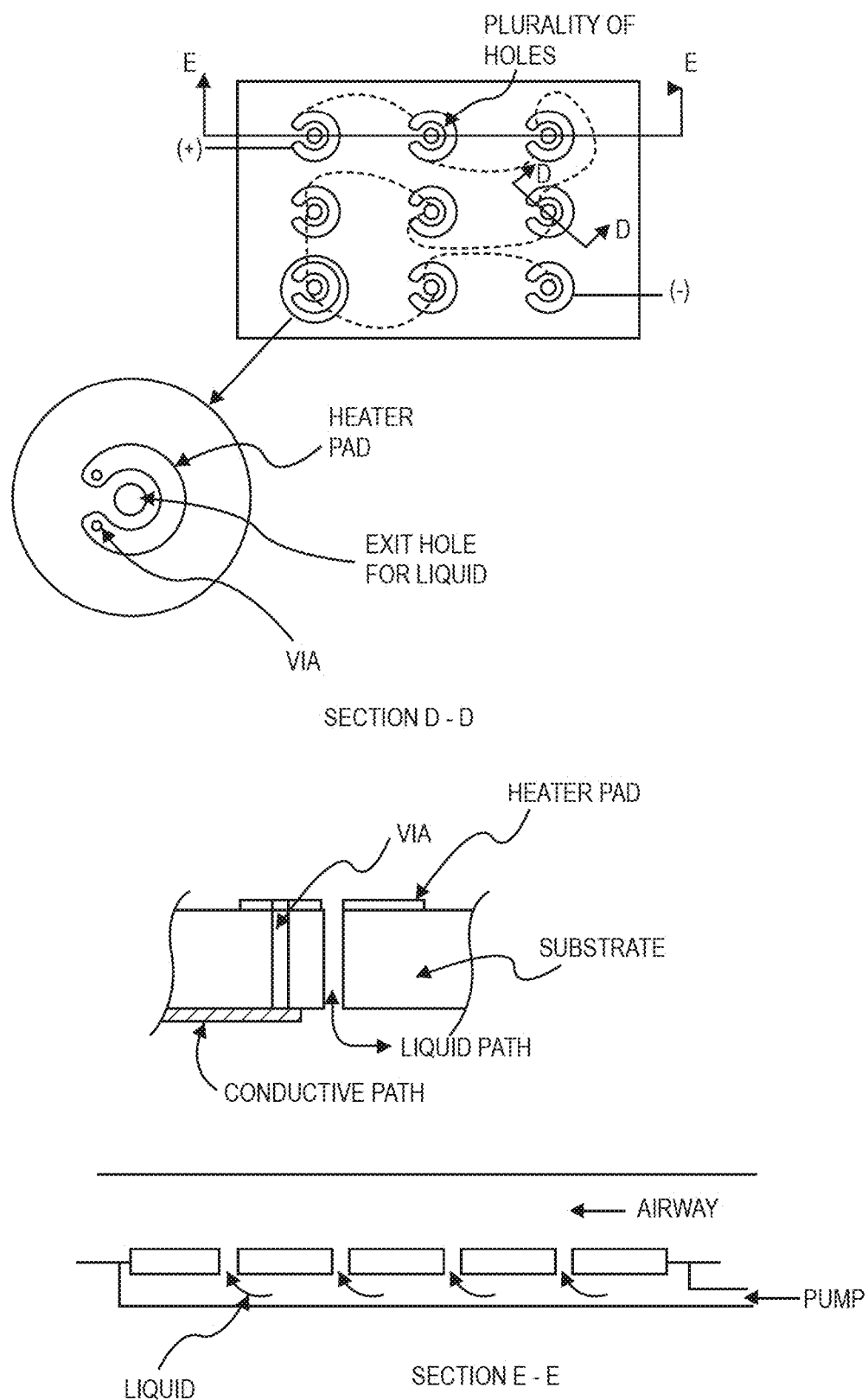
FIG. 36 demonstrates an example of a heater fabricated using

FIG. 34 shows a heating element made from a thin metallic foil. Holes may be made in the foil through a method such as punching, etching, or cutting (e.g., laser cutting). These holes may serve two advantageous purposes. The holes in the metallic foil may increase the electrical resistance of the heating element and liquid may be pumped through the holes. In one side of the heater may be a gas flow channel that carries away the aerosolized or vaporized liquid and on the other is the liquid flow channel to convey the liquid to the heating element. FIG. 35 shows a liquid flow channel that may be formed by punching holes in a metallic foil in such a way that this causes a raised channel which conveys the liquid to the heating element or to a porous material on the back side of the heating element.

FIG. 36 shows a heating element and liquid flow channel that may be made using circuit board fabrication methods. The board may have a plurality of small holes in it. For example, the number of holes may be about 100 or about 1000 and the size of the holes may range between about 0.001 inches (in) and about 0.01 in. In the top layer of the board, and positioned around the holes may be a heating element. Current may be routed from one hole to the next in a serial manner by use of vertical interconnect access (via)'s to the bottom surface of the board. The board may be made from a material (such as Kapton) that can withstand the required temperature (approximately 350° C.).

An aerosol or vapor drug delivery device may comprise a gas flow channel that carries a pharmaceutical compound or pharmaceutical composition to a subject. A gas flow channel may comprise one or more inlets and one or more outlets. A gas flow channel may primarily transport air or other gases. A gas flow channel may be operatively connected to one or more sources of propellants or compressed gases that cause gas flow in the gas flow channel. A gas flow channel may comprise one or more sections of tubing or piping. A gas flow channel may comprise a molded or fabricated section of the device housing. A gas flow channel may comprise materials such as polymers, metals, ceramics, and glasses.

An aerosol or vapor drug delivery device may comprise a housing. A housing may comprise one or more pieces that serve to secure and enclose the components of the aerosol or vapor drug delivery device. A housing may comprise materials such as polymers, metals, ceramics, and glasses. A housing may contain one or more windows for viewing the liquid level in a reservoir. The housing may comprise one or more ports for establishing electrical or fluid connectivity with the drug delivery device. A housing may comprise one or more digital or analog displays, e.g., number of doses remaining. A housing may comprise various buttons and switches for control of the drug delivery device. A housing may be designed to be leakproof, waterproof, or resistant to breakage. A housing may be formed by injection molding.

Vaporizer Devices

In an aspect, the present disclosure provides, as illustrated in FIGS. 47-49, a vaporizer device 4600 comprising a reservoir 4840, a dispenser 4360, and a heater 4320. In some embodiments, the reservoir 4840 is configured to contain a medicament. In some embodiments, the reservoir 4840 comprises a seal 4370. In some embodiments, the seal 4370 is configured to contain the medicament within the reservoir 4840. In some embodiments, the medicament comprises a formulation, an active pharmaceutical ingredient, an extract, or any combination thereof. In some embodiments, the medicament is a fluid. in some embodiments, the medicament is a liquid. In some embodiments, the reservoir 4840 is formed of a material that is inert to the medicament.

In some embodiments, the dispenser 4360 is configured to receive the medicament pumped from the reservoir 4840. In some embodiments, as illustrated in FIGS. 48A and 48B, the dispenser 4360 comprises an extract inlet port 4362B configured to receive the medicament pumped from the reservoir 4840. In some embodiments, the dispenser 4360 comprises two or more extract inlet ports 4362B. In some embodiments, the dispenser 4360 has an outer surface 4365. In some embodiments, the outer surface 4365 of the dispenser 4360 comprises an aperture 4366. In some embodiments, the outer surface 4365 of the dispenser 4360 comprises an array of apertures 4366. In some embodiments, the dispenser 4360 comprises a regular array of apertures 4366 arranged thereabout, wherein the apertures 4366 are arranged with equal separations therebetween about the outer surface 4365. In some embodiments, the regular array of apertures 4366 comprises a radial array of apertures 4366, wherein the apertures 4366 are arranged about an axis. In some embodiments, two or more of the apertures 4366 in the regular array of apertures 4366 are congruent. In some embodiments, the dispenser 4360 is formed of a thermally stable material comprising metal, glass, ceramic, plastic, or any combination thereof. In some embodiments, the dispenser 4360 comprises a first dispenser 4361 and a second dispenser 4362. In some embodiments, the first dispenser 4361 has a surface comprising an array of first slots 4361A. In some embodiments, the second dispenser 4362 has a surface comprising an array of second slots 4362A. In some embodiments, the array of first slots 4361A and the array of second slots 4362A interdigitate. In some embodiments, the first dispenser 4360 and the second dispenser 4360 form a cavity therebetween. In some embodiments, the cavity is an open cavity. In some embodiments, the outer surface 4365 of the dispenser 4360 is an outer surface of the first dispenser 4361. In some embodiments, the outer surface 4365 of the dispenser 4360 is an outer surface of the first dispenser 4362. In some embodiments, the first dispenser 4361 comprises a plurality of notches 4361B that accept the first heating coil 4321 and the second heating coil 4322. In some embodiments, the plurality of notches 4361B are on an outer edge of the first dispenser 4361.

In some embodiments, the heater 4320 at least partially surrounds at least a portion of the dispenser 4360. In some embodiments, the heater 4320 completely surrounds the dispenser 4360. In some embodiments, the heater 4320 surrounds the first dispenser 4360, the second dispenser 4360, or both. In some embodiments, the heater 4320 is configured to heat the medicament received by the dispenser 4360. In some embodiments, the heater 4320 is formed of a conductive metal, wherein applying a voltage to the heater 4320 heats the medicament received by the dispenser 4360. In some embodiments, the heater 4320 is configured to vaporize the medicament received by the dispenser 4360. In some embodiments, the heater 4320 comprise a helical heater 4320, wherein the heater 4320 has a spiral shape. In some embodiments, the helical heater 4320 comprises two or more helical coils. In some embodiments, the two or more helical coils are interdigitated. In some embodiments, the two or more helical coils overlap. In some embodiments, the helical heater 4320 has a diameter of about 0.006 inches to about 0.008 inches. In some embodiments, the helical heater 4320 has a length of about 25 inches to about 75 inches. In some embodiments, the helical heater 4320 has a working voltage of about 3 volts to about 9 volts. In some embodiments, the helical heater 4320 has a working power of about 5 watts to about 50 watts. In some embodiments, the helical heater 4320 has two or more helical revolutions.

In some embodiments, the vaporizer device 4600 further comprises a housing comprising a first inlet and an outlet, wherein the housing is configured to direct a fluid from the inlet, through the heater 4320, and to the outlet. In some embodiments, the housing further comprises a second inlet configured to isolate at most a portion of the fluid from the heater 4320. In some embodiments, the first inlet and the second inlet, individually or in combination, have a cross sectional area of at least about 50 mm$^2$.

In some embodiments, the vapor device 4600 further comprises a valve coupled to an outlet of the reservoir 4840. In some embodiments, at least a portion of the valve is surrounded by the heater 4320, the dispenser 4360, or both. In some embodiments, the valve comprises a pressure release valve in a direction from the reservoir 4840 to the outlet. In some embodiments, the pressure relieve valve is resealable.

In some embodiments, the vaporizer device 4600 further comprises a preheater configured to heat the medicament in the reservoir 4840, the medicament in the dispenser 4360, or both. In some embodiments, at least a portion of the preheater is at least partially surrounds the reservoir 4380. In some embodiments, the vaporizer device 4600 further comprises a mouthpiece 4330.

In some embodiments, the vaporizer device 4600 is capable of emitting at least about 5 mg/second of the medicament. In some embodiments, the vaporizer device 4600 is capable of forming an aerosol particle of the medicament having a size of greater than about 1 μm. In some embodiments, the vaporizer device 4600 does not comprise a wick. In some embodiments, the vaporizer device 4600 further comprises an actuator configured to pump the medicament from the reservoir 4840.

Figure 46:
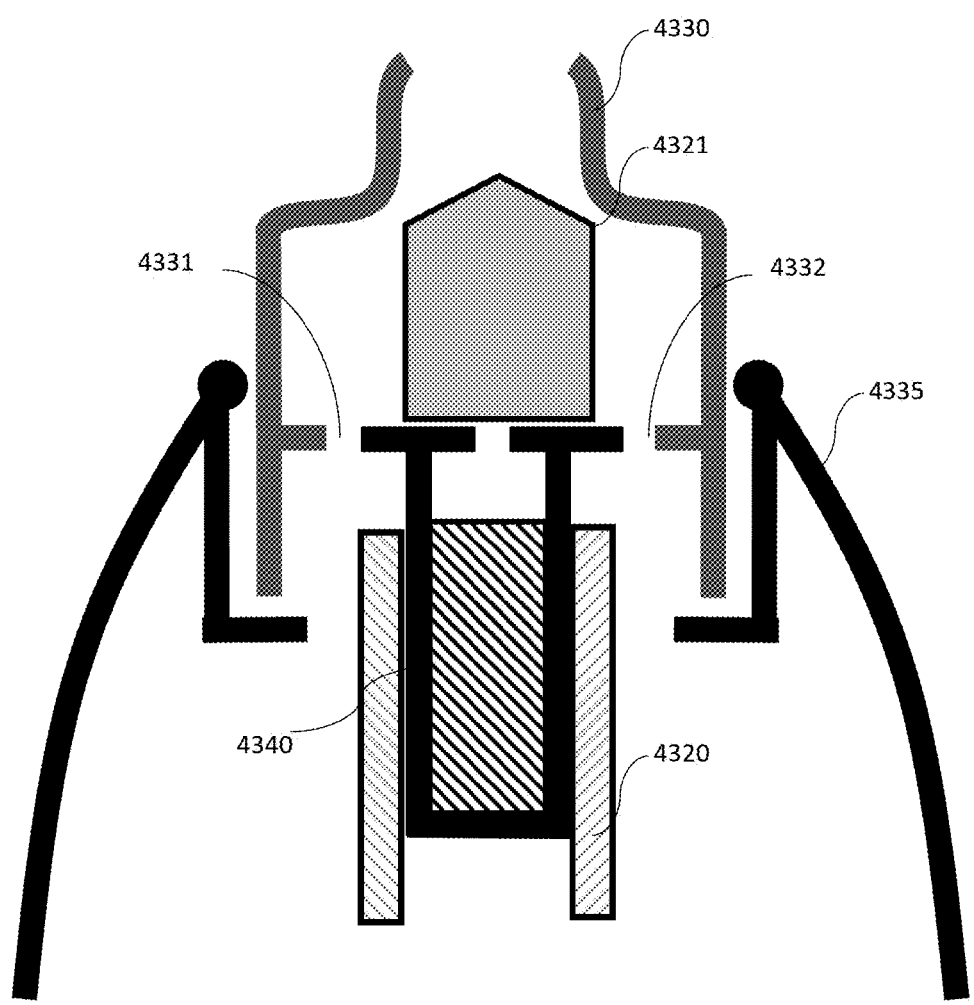

As shown in FIG. 46, another example device comprises a renewable component, e.g., a dose cartridge, that can be replaced after use. The dose cartridge contains a mouthpiece 4330, a vaporization element 4321, a first air inlet 4331, a second air inlet 4332, a reservoir 4380 (e.g., a syringe housing) and its outer shell 4340. The dose cartridge may be configured to be received by a controller 4335. The device may comprise a plurality of heating elements 4320 that couples to the outer shell 4340 that can heat up the compounds contained in the reservoir 4380. The heating elements 4320 may be made of thin film etched metal elements on an electrically insulating substrate such as Kapton, free standing tongs electrically resistive metal such as Nichrome or stainless steel, etc. In some embodiments, the heating elements 4320 comprise a metallic wire. A temperature sensor may be used to measure and control the temperature of the reservoir 4380 (e.g., syringe housing).

Vaporizing Base Device

Figure 49:
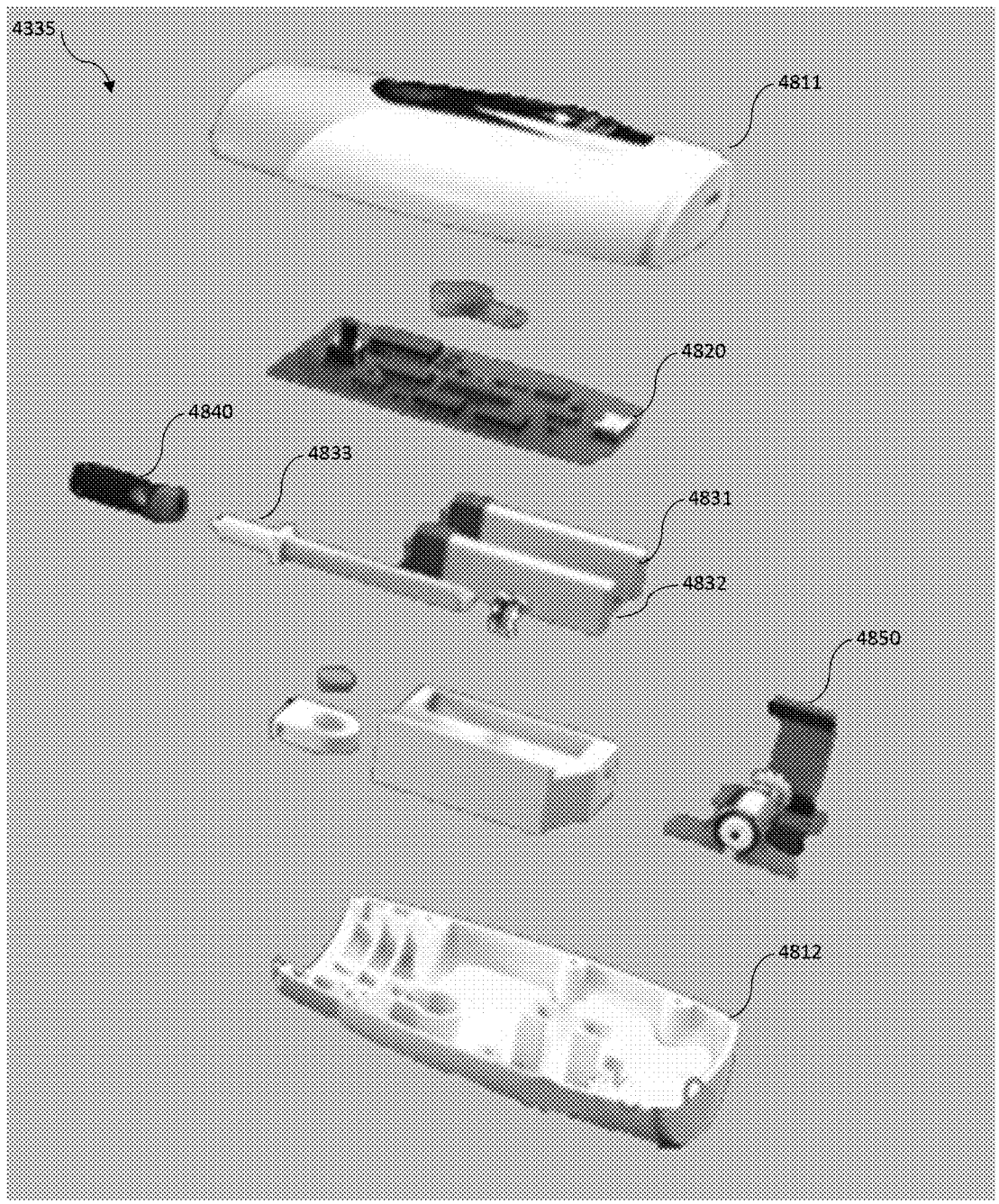
FIG. 49 depicts another example exploded schematic of an embodiment of an aerosol drug delivery device.

In another aspect, the present disclosure provides, as illustrated in FIG. 49, a vaporizer assembly comprising: the vaporizer device 4600 herein and a vaporizing base device 4335 comprising an actuator 4833 configured to pump the medicament from the reservoir 4840. In some embodiments, the actuator 4833 comprises a motor, a spring, a compressed fluid container, a chemical expander, a peristaltic pump, or any combination thereof. In some embodiments, the vaporizer device 4600 is controlled by the vaporizing base device 4335.

As illustrated in FIG. 49, the vaporizing base device comprises a first shell portion 4811, a second shell portion 4812, a printed circuit board (PCB) 4820, a first battery 4831, a second battery 4832, a pump drive 4833, a capsule of the pharmaceutical compositions provided herein 4840, and a motor 4850. In some embodiments, the motor 4850 comprises a stepper motor. In some embodiments, the controller 4335 does not comprise the second battery 4832.

Computing Systems

Figure 37:
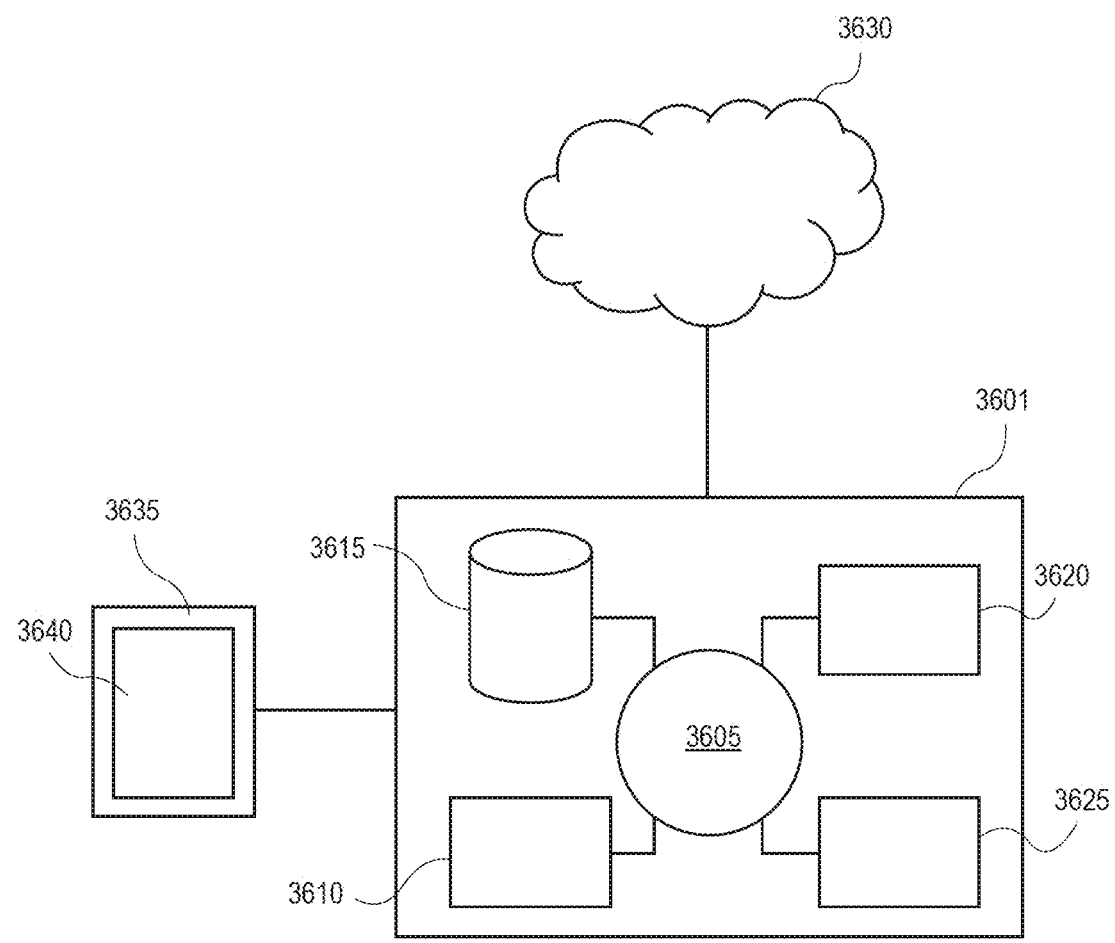

The present disclosure provides computer systems that are programmed to implement methods of the disclosure. FIG. 37 shows a computer system 3601 that is programmed or otherwise configured to control an electronic drug delivery device. The computer system 3601 can regulate various aspects of drug delivery of the present disclosure, such as, for example, adjusting the rotary pump speed based upon the detected viscosity of the pumped fluid. The computer system 3601 can be an electronic device of a user or a computer system that is remotely located with respect to the electronic device. The electronic device can be a mobile electronic device.

The computer system 3601 includes a central processing unit (CPU, also "processor" and "computer processor" herein) 3605, which can be a single core or multi core processor, or a plurality of processors for parallel processing. The computer system 3601 also includes memory or memory location 3610 (e.g., random-access memory, read-only memory, flash memory), electronic storage unit 3615 (e.g., hard disk), communication interface 3620 (e.g., network adapter) for communicating with one or more other systems, and peripheral devices 3625, such as cache, other memory, data storage and/or electronic display adapters. The memory 3610, storage unit 3615, interface 3620 and peripheral devices 3625 are in communication with the CPU 3605 through a communication bus (solid lines), such as a motherboard. The storage unit 3615 can be a data storage unit (or data repository) for storing data. The computer system 3601 can be operatively coupled to a computer network ("network") 3630 with the aid of the communication interface 3620. The network 3630 can be the Internet, an internet and/or extranet, or an intranet and/or extranet that is in communication with the Internet. The network 3630 in some cases is a telecommunication and/or data network. The network 3630 can include one or more computer servers, which can enable distributed computing, such as cloud computing. The network 3630, in some cases with the aid of the computer system 3601, can implement a peer-to-peer network, which may enable devices coupled to the computer system 3601 to behave as a client or a server.

The CPU 3605 can execute a sequence of machine-readable instructions, which can be embodied in a program or software. The instructions may be stored in a memory location, such as the memory 3610. The instructions can be directed to the CPU 3605, which can subsequently program or otherwise configure the CPU 3605 to implement methods of the present disclosure. Examples of operations performed by the CPU 3605 can include fetch, decode, execute, and writeback.

The CPU 3605 can be part of a circuit, such as an integrated circuit. One or more other components of the system 3601 can be included in the circuit. In some cases, the circuit is an application specific integrated circuit (ASIC).

The storage unit 3615 can store files, such as drivers, libraries, and saved programs. The storage unit 3615 can store user data, e.g., user preferences and user programs. The computer system 3601 in some cases can include one or more additional data storage units that are external to the computer system 3601, such as located on a remote server that is in communication with the computer system 3601 through an intranet or the Internet.

The computer system 3601 can communicate with one or more remote computer systems through the network 3630. For instance, the computer system 3601 can communicate with a remote computer system of a user (e.g., the subject for a drug delivery device). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 3601 via the network 3630.

Methods as described herein can be implemented by way of machine (e.g., computer processor) executable code stored on an electronic storage location of the computer system 3601, such as, for example, on the memory 3610 or electronic storage unit 3615. The machine executable or machine readable code can be provided in the form of software. During use, the code can be executed by the processor 3605. In some cases, the code can be retrieved from the storage unit 3615 and stored on the memory 3610 for ready access by the processor 3605. In some situations, the electronic storage unit 3615 can be precluded, and machine-executable instructions are stored on memory 3610.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 3601, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semi-conductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical, and electromagnetic waves, such as used across physical interfaces between local devices, through wired and optical landline networks and over various air-links. The physical elements that carry such waves, such as wired or wireless links, optical links, or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 3601 can include or be in communication with an electronic display 3635 that comprises a user interface (UI) 3640 for providing, for example, drug delivery and device control options. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 3605. The algorithm can, for example, determine the fluid viscosity and modulate the output of heating elements to adjust the fluid properties.

EXAMPLES

Example 1—Exemplary Aerosol Delivery Device

Aerosols for respiratory drug delivery can be generated using a handheld device. The device may be intended for medical use, medicinal use, recreational use, or combinations thereof. The device contains a user interface intended for permitting control and display of dosing history and dose control. The device comprises a body with an integrated screen, control buttons, a mouthpiece with an inhalation port, and a cap. The screen may be curved or flat, with backlighting, data display, and security measures. The device further comprises a cartridge containing a fluid compound. The device also comprises an aerosol generation mechanism and a power source. The power source may be a rechargeable battery or replaceable battery. An aerosol delivery device with a rechargeable battery may also have a charge port such as a Micro USB port. The charge port may also permit external connections to the user interface, for example for uploading dosage controls.

Figure 38A:
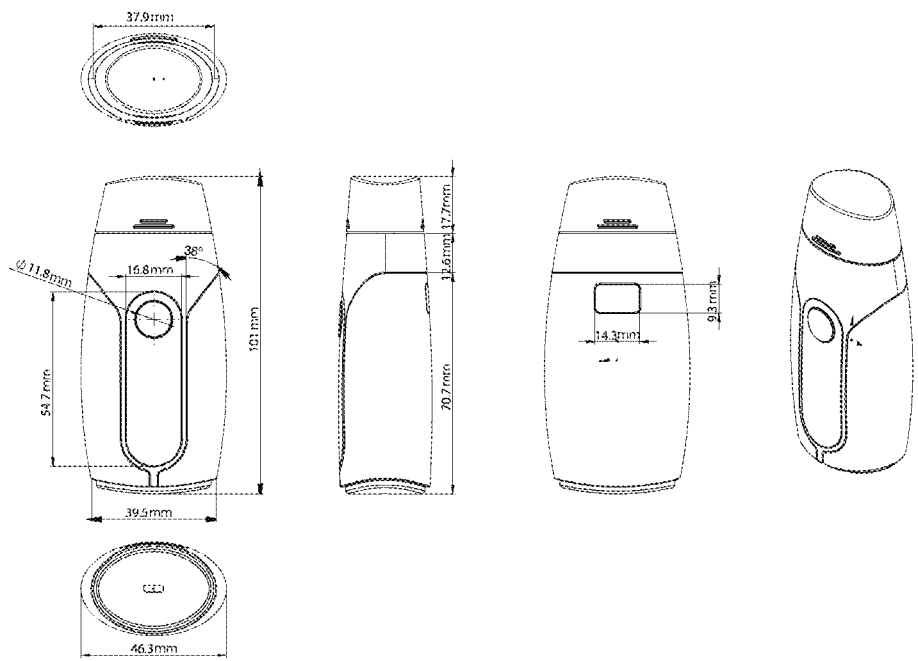
Figure 38B:
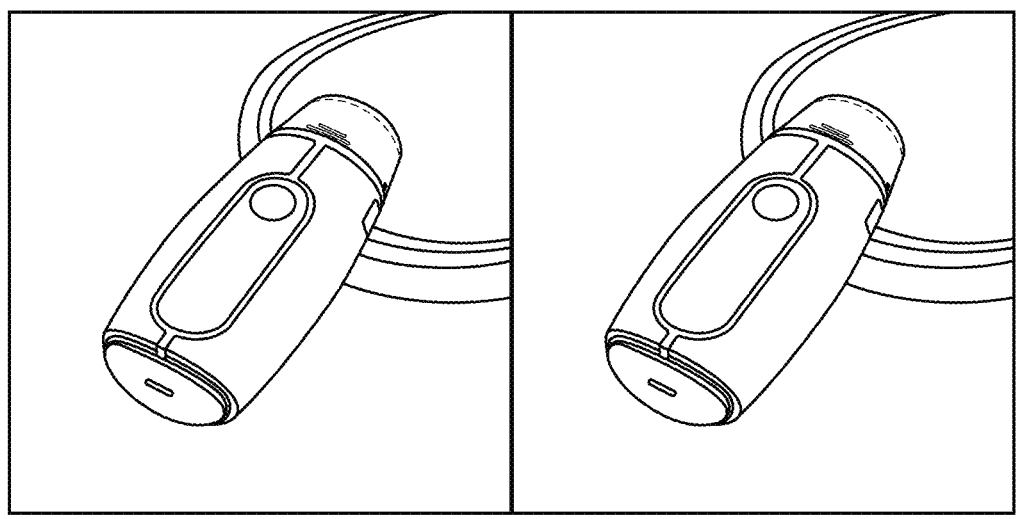

FIG. 38A shows illustrations of a first device form factor with front, side, back, and isometric views displayed. FIG. 38B displays photographs of devices produced with the first form factor. FIG. 39A shows illustrations of a second device form factor with front, side, back, and isometric views displayed. FIG. 39B displays photographs of devices produced with the second form factor.

Example 2—Dose Cartridge Reservoirs

An aerosol delivery device, such as those described herein, may contain a syringe-type reservoir. For the product to be able to be shipped and to have a reasonable shelf life, the reservoir, in this case the interior of the syringe, needs to be able to be sealed upon loading of the formulation. To do this the syringe is manufactured with the outlet of the syringe sealed with a breakable seal that ruptures upon the syringe pump drive exerting sufficient pressure on the seal. This seal may be a section of plastic witch has been relieved or weakened by a thinning, or narrowing, of the seal (such that it ruptures with sufficient force). To fill the syringe with formulation, vacuum may be applied to the interior of the syringe, removing the majority of the air from the interior. Formulation may then be pumped into the reservoir. Subsequently, the entry point may be sealed by a method such as heat sealing or any other suitable methods.

Example 3—Reservoir Drive Element

The aerosol delivery device containing a dose cartridge comprises a syringe reservoir and a plunger. The element of the syringe pump that drives the plunger may be located in the reusable part of the product. The plunger of the syringe may be mated to a drive element in case at the end of an inhalation the syringe pump drive needs to pull back on the plunger to preclude unwanted formulation to be expressed. The plunger may be connected to a drive element with a mating clasp (ball and socket) or other suitable component between the plunger and the drive element. Alternatively, a magnet may be located on the drive element and a metal component may be located on the plunger.

Figure 40A:
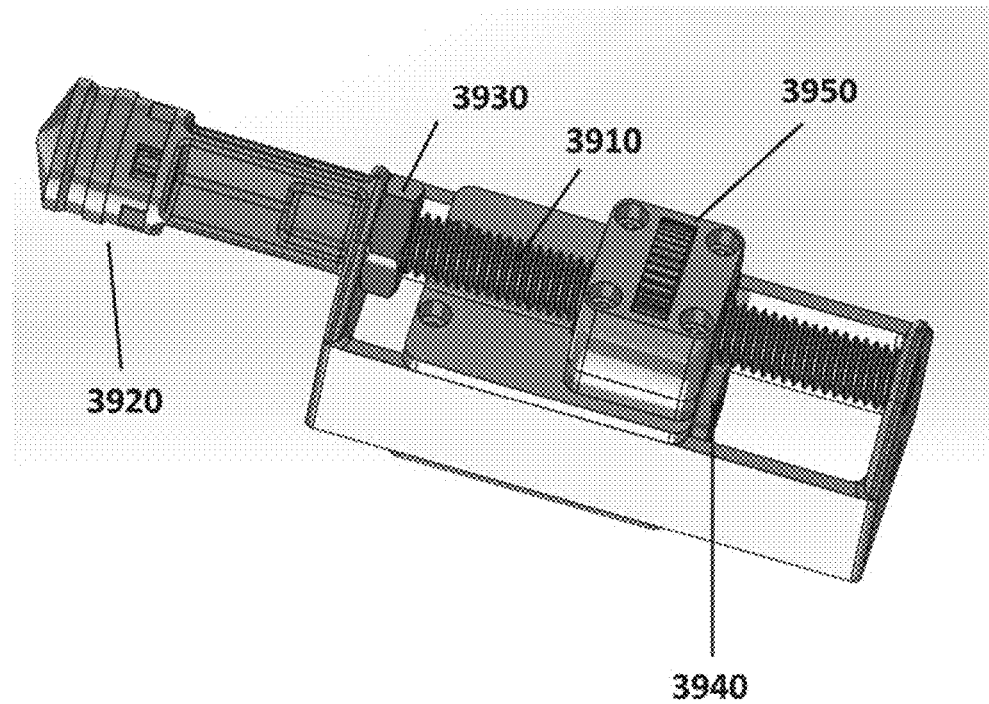
Figure 40B:
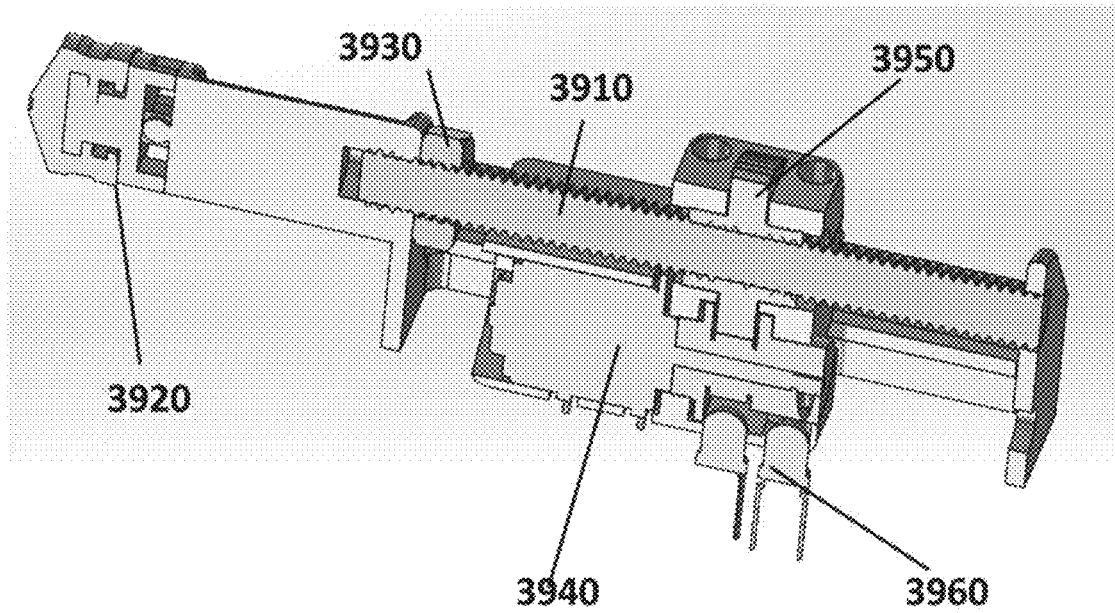

FIG. 40A shows an illustration of a lead screw drive element 3910 coupled to syringe plunger 3920 by a mating clasp 3930. The lead screw 3910 is driven by a stepper motor 3940 that is coupled to a gear 3950 that mates with the lead screw 3910. FIG. 40B shows a cross-section of the drive element configuration shown in FIG. 40A.

Figure 41A:
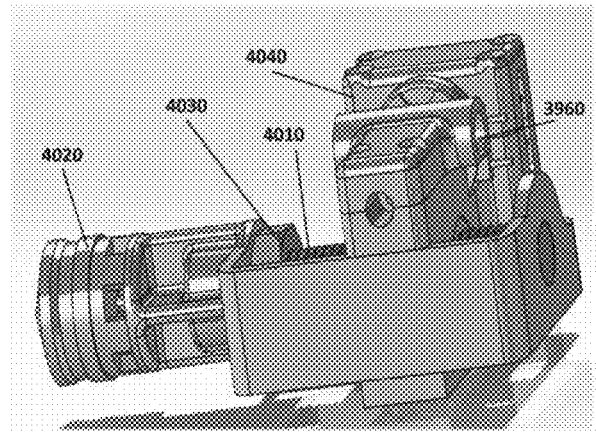
Figure 41B:
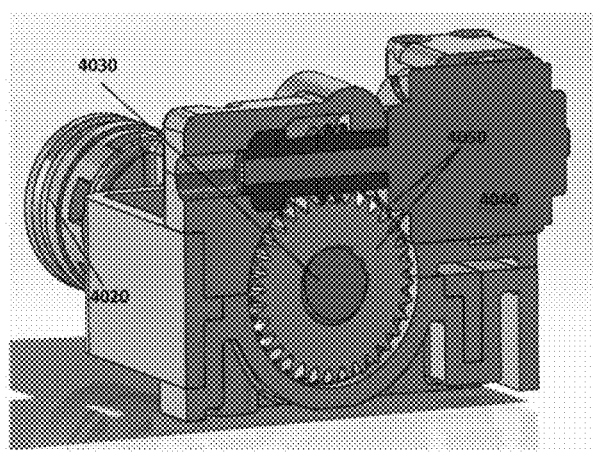
Figure 41C:
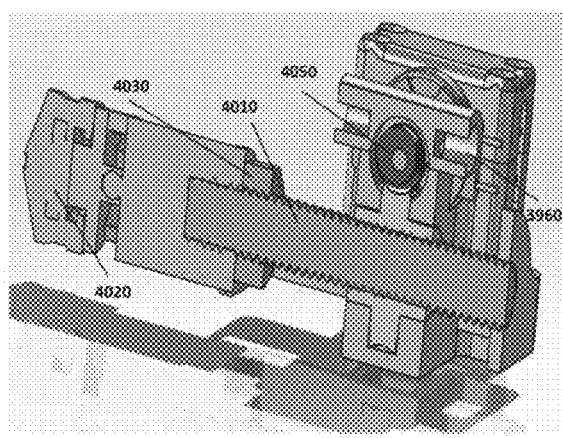

FIG. 41A shows an illustration of a second drive element configuration. A lead screw 4010 is coupled to a syringe plunger 4020 by a mating clasp 4030. The lead screw 4010 is coupled to a worm gear 4050 that is turned by a stepper motor 4040. FIGS. 41B and 41C depict cross-sectional views of the lead screw 4010 driven by the worm gear 4050.

Example 4—Position Sensing

An aerosol delivery device may contain a position sensing apparatus to accurately determine when the drive element has mated to the syringe plunger. Upon a dose cartridge being inserted into the reusable part of the product, the drive may locate the syringe plunger and properly mate to it. The aerosol delivery device may contain a position sensing apparatus that determines the position of the lead screw. FIGS. 40B and 41A show an LED/light detector pair 3960 where the optical path between the plunger and the drive element is interrupted a number of times per revolution of the stepper motor. Detection of the number of revolutions of the stepper motor allows the device to measure the speed of the stepper motor. The stepper motor is driven forward with a low force until the stepper motor has stopped thereby indicating that the drive and the plunger are mated.

Example 5—On-Axis Dispensing Method

Figure 42A:
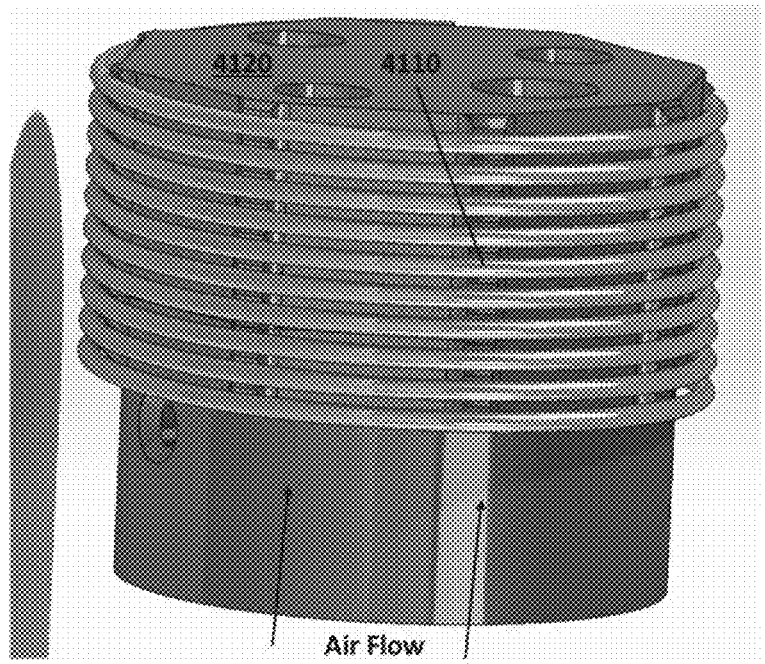
Figure 42B:
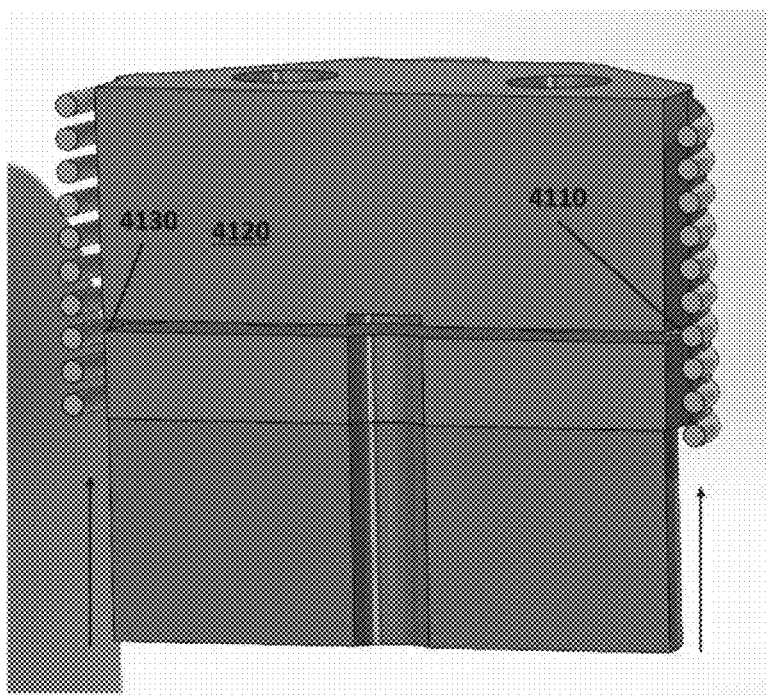

An aerosol delivery device may contain a dispensing system that transfers fluid from a reservoir to a heating element to permit aerosol formation. FIG. 42A shows an illustration of a fluid dispenser with an "on-axis" design relative to the heating element. The heater element 4110 is wrapped around a high temperature plastic, or a ceramic member 4120 that is used to dispense the formulation through dispensing ports 4130 onto the heater element 4110 and to hold the heater element in position. The heater element 4110 may be made with other suitable material that can withstand high temperature. FIG. 42B shows a cross-section of the dispensing system shown in FIG. 42A where the position of the dispensing ports 4130 can be seen relative to the heating element 4110.

Example 6—Side Dispensing Method

Figure 43A:
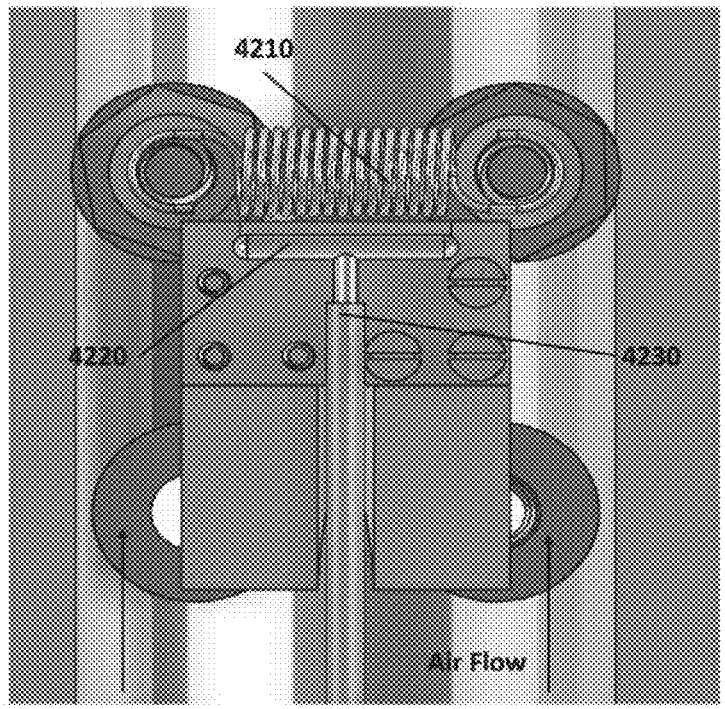
Figure 43B:
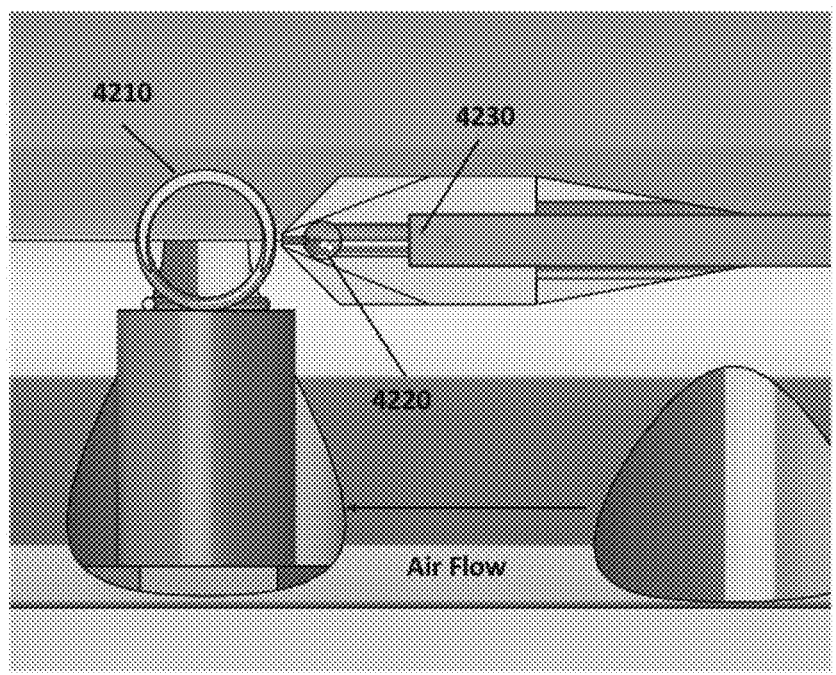

An aerosol delivery device may contain a dispensing system that transfers fluid from a reservoir to a heating element to permit aerosol formation. FIG. 43A shows a top-down illustration of a fluid dispenser with a side-oriented design relative to the heating element. The heater element 4210 is a coil (helix) of electrically resistive wire (titanium or nichrome or other suitable materials) suspended in air across the airway 4220 and in front of (downstream of) the dispensing element 4230. The dispensing element 4230 is made of a metallic, ceramic, or high temperature silicone and is used to spread the formulation out into a line and in that way the formulation is dispensed onto the edge of the heater element 4210. FIG. 43B shows a side-view of the dispensing system shown in FIG. 43A.

Example 7—Particle Size as a Method to Control Use of a Pharmaceutical Composition In the current market, devices that are used to generate an aerosol for inhalation may have a drawback in that they product an aerosol that has a particle size where a large proportion of the aerosol does not deposit in the respiratory tract and is exhaled making the exhaled aerosol visible. Aerosols from some vaping devices have particle sized in the 0.4-0.9-micron range (see data below, Table #1) and are too light to gravitationally settle or impact in the lung and are subsequently exhaled. As such, the devices and systems herein form aerosols with a particle size of greater than about 1 micron. When a proportion of the aerosol is exhaled it is both seen and smelt by others. This is often not optimal as the vape user may wish to not draw attention to themselves. Some vaping devises vaporize around 1.0-1.5 mg/sec (see data below) and because of the small cross section on their airway (e.g., 10 to 15 mm$^2$) mix the vaporized compound into the entirety of the inhaled air.

TABLE 1

Examples of aerosol particle size

| Product | Inhalation flow rate (lpm) | Visual Mean Aerodynamic Diameter (μm) | Geometric Standard Deviation of the width of the aerosol particle disc |
| --- | --- | --- | --- |
| Stiiizy pod system | 1.5 | 0.95 | 1.75 |
|  | 3.25 | 0.9 | 1.6 |
|  | 6 | 0.8 | 1.6 |
|  | 10 | 0.7 | 1.4 |
| Example 510 thread pod system | 2.5 | 0.9 | 1.6 |
|  | 3 | 085 | 1.6 |

Figure 44:
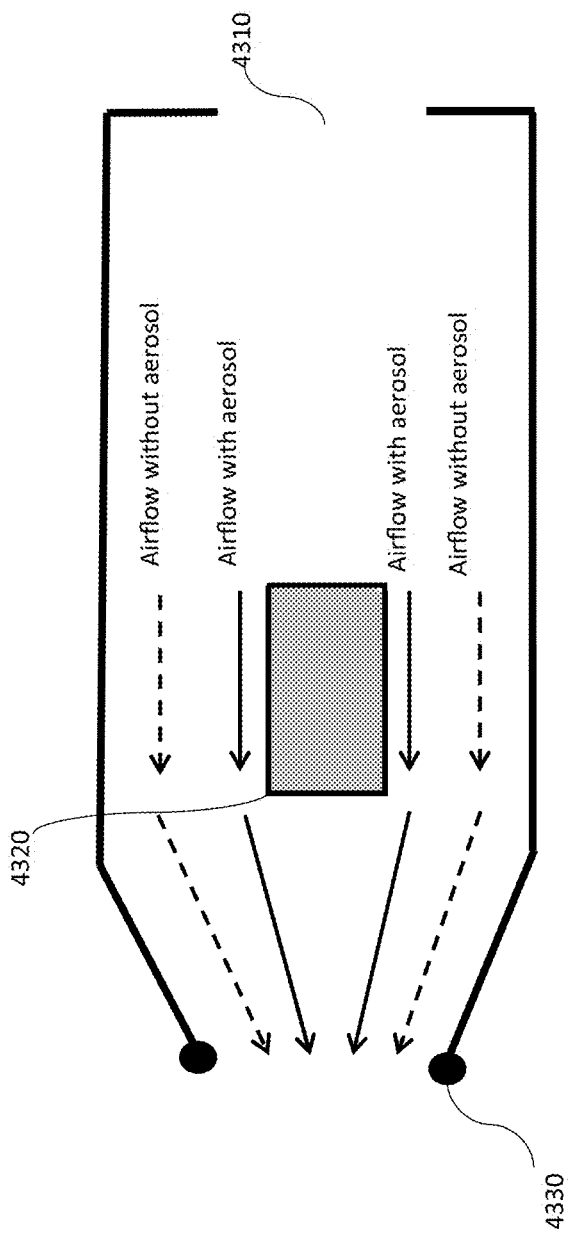
Figure 45:
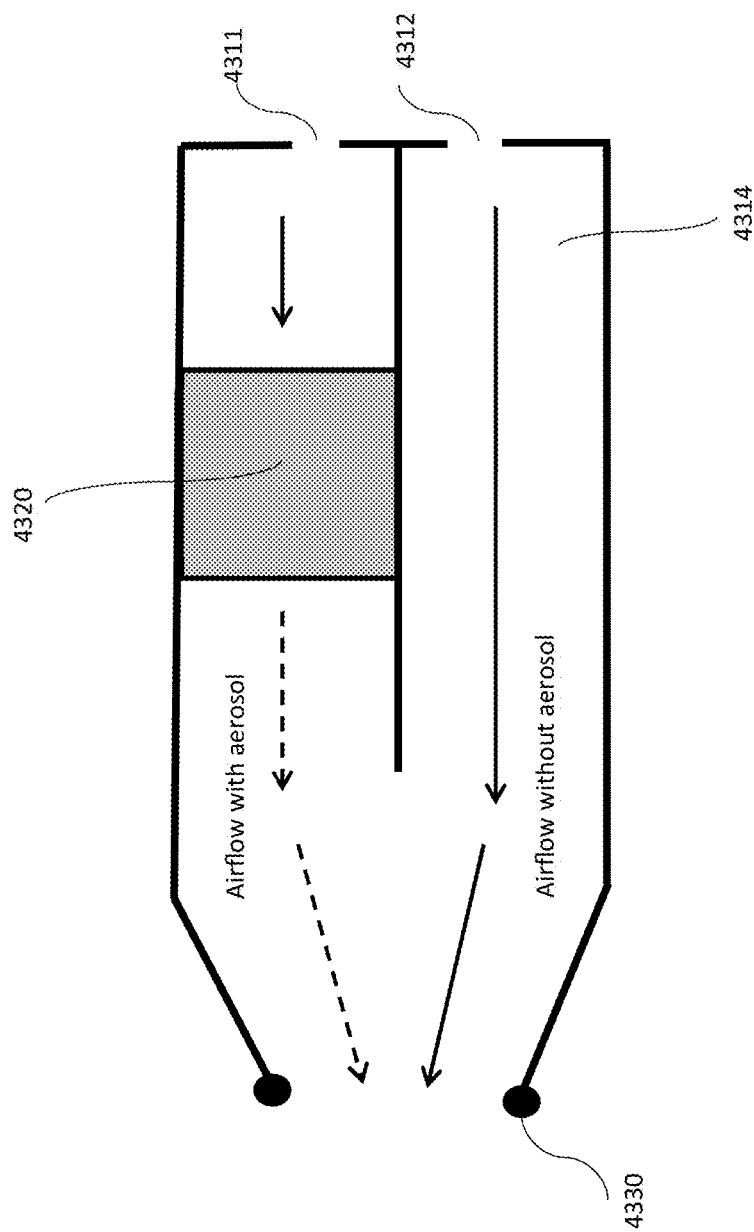

In some embodiment, the device disclosed herein comprises a housing (4314) as showing in FIGS. 44 and 45. The housing 4314 comprises a primary inlet 4311 and a secondary inlet 4312 illustrated in FIG. 45 and surrounds a medicament released as an aerosol 4320. In some embodiments, the primary inlet and the secondary inlet have a combined cross-sectional area of at least about 40 nm² to about 400 nm². In some embodiments, the primary inlet and the secondary inlet have a combined cross-sectional area of at least about 50 nm² to about 250 nm². In some embodiments, the primary inlet and the secondary inlet have a combined cross-sectional area of about 200 nm². Further, the housing 4314 comprises an outlet.

The current example provides an embodiment of the device disclosed herein that provides a larger cross-sectional area of the airway to increase aerosol particle size. In one embodiment, the device disclosed herein can produce 10 mg/sec of vapor of the pharmaceutical composition disclosed herein. The cross sectional area of the airway in FIGS. 44 and 45 is about 200 mm² and the majority of vaporized compound in mixed into a small percentage of the inhaled air that is moving through the airway. The majority of the air traveling through the inlet 4310 goes around the location that the compound is being vaporized 4320 and out a mouthpiece 4330, as shown in FIG. 44.

Figure 50:
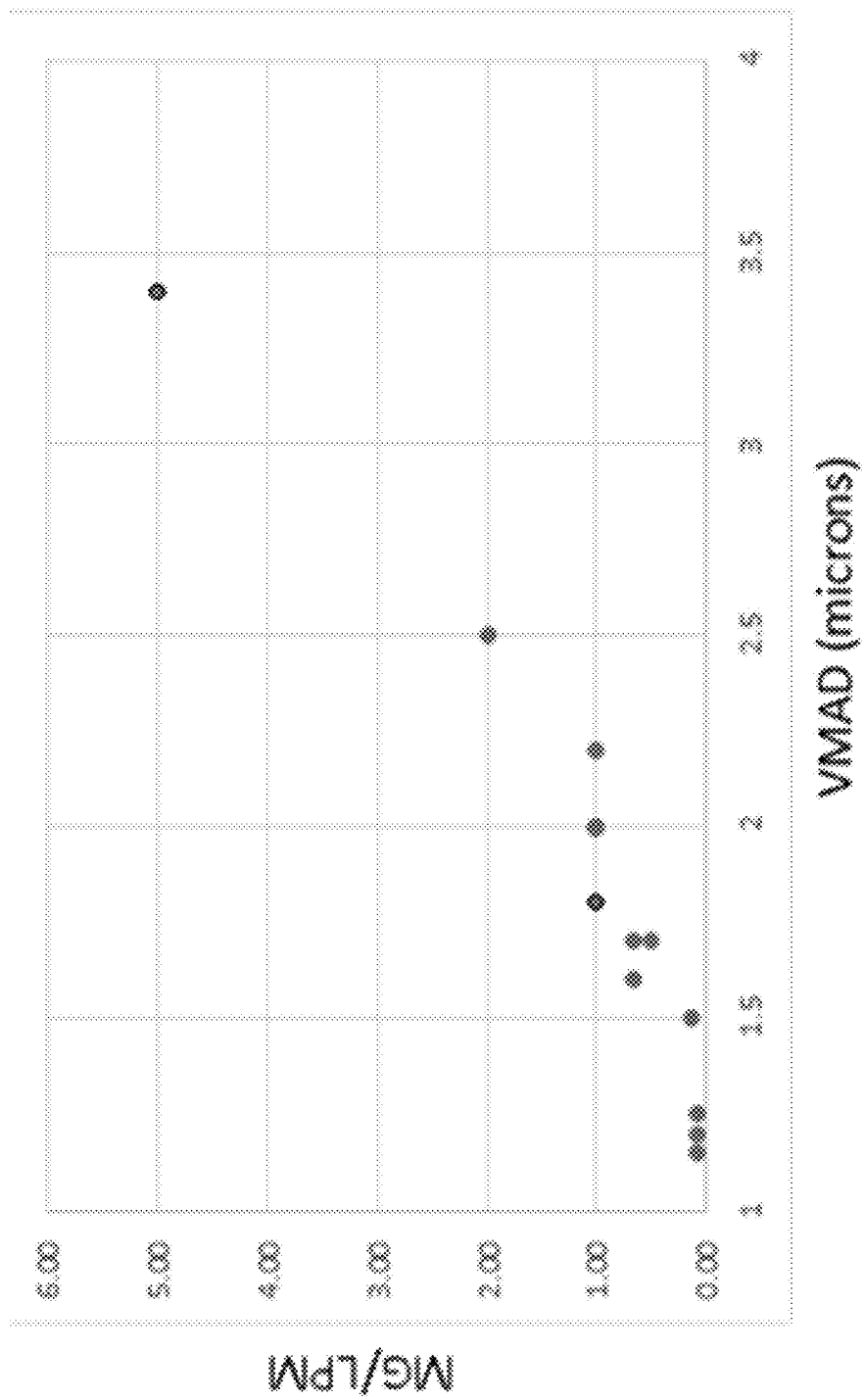
FIG. 50 shows aerosol particle size as a function of a ratio of the mass of the pharmaceutical compound vaporized to an inhalation flow rate.

As shown in FIG. 50, aerosol particle sizes may be controlled by a variety of factors, such as an inhalation flow rate of the aerosol generating device, the amount of composition disposed to be vaporized, etc. FIG. 50 demonstrates aerosol particle size as a function of the ratio of the mass of the compound vaporized to the inhalation flow rate.

Further, in some embodiments as illustrated in FIG. 45, a portion of the inhaled air 4313 may be routed around the vaporization chamber 4320 and mixed with the air containing the aerosol downstream. The mixing occurs when the aerosol has reached a relatively stable aerosol size, e.g., the aggregation rate of the aerosol has decreased substantially. Mixing of the bulk of the inhaled air back into the portion of the inhaled air contains the aerosol causes the aerosol aggregation rate to decrease further, thereby generating aerosol with larger particle sizes compared the aerosol particle sizes generated by the aerosol generating devices available in the market. The aerosol with larger particle sizes tend to deposit in the respiratory tract of an inhaler and is not exhaled when the inhaler inhales the aerosol in. As a result, the amount of exhaled aerosol is greatly reduced and enables concealed use of the aerosol generating device.

Example 8—Preheating Ultra-Thick Extracts Prior to Pumping

Certain cannabinoid extracts such as those called "Budder, Badder, Sugar, THCa Powder, Distillate, Rosin, Thick sauces" may have a high viscosity at room temperature. As such these extracts are difficult to pump from the syringe pump. In some embodiments, the device disclosed herein is used to preheat these compounds to a temperature wherein the viscosity is lowered to a point where pumping can occur. The preheating temperature ranges from about 35 to about 45 C.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations, or equivalents. It is intended that the following claims define the scope of the invention and that methods and structures within the scope of these claims and their equivalents be covered thereby.

What is claimed is:

1. A vaporizer device comprising:
   (a) a reservoir configured to contain a medicament;
   (b) a dispenser having an outer surface, wherein the outer surface comprises a regular array of apertures arranged thereabout, and wherein the dispenser is configured to receive the medicament pumped from the reservoir, wherein the dispenser comprises:
      (i) a first dispenser portion having a surface comprising an array of first slots; and
      (ii) a second dispenser portion having a surface comprising an array of second slots, wherein the array of first slots and the array of second slots interdigitate; and
   (c) a heater, wherein the heater at least partially surrounds at least a portion of the dispenser, wherein the heater is configured to heat the medicament received by the dispenser.

2. The vaporizer device of claim 1, wherein the regular array of apertures comprises a radial array of apertures.

3. The vaporizer device of claim 1, wherein the apertures in the regular array of apertures are congruent.

4. The vaporizer device of claim 1, wherein the dispenser is formed of a thermally stable material comprising metal, glass, ceramic, plastic, or any combination thereof.

5. The vaporizer device of claim 1, wherein the first dispenser portion and the second dispenser portion form an open cavity therebetween.

6. The vaporizer device of claim 1, wherein the reservoir comprises a seal configured to contain the medicament within the reservoir.

7. The vaporizer device of claim 1, wherein the heater comprises a helical heater.

8. The vaporizer device of claim 7, wherein the helical heater comprises two or more helical coils.

9. The vaporizer device of claim 7, wherein the helical heater has:
   (a) a diameter of about 0.006 inches to about 0.008 inches;
   (b) a length of about 25 inches to about 75 inches;
   (c) a working voltage of about 3 volts to about 9 volts;
   (d) a working power of about 5 watts to about 50 watts;
   (e) two or more helical revolutions; or
   (f) any combination thereof.

10. The vaporizer device of claim 1, wherein the heater is configured to vaporize the medicament received by the dispenser.

11. The vaporizer device of claim 1. further comprising a housing comprising a first inlet and an outlet, wherein the housing is configured to direct a fluid from the first inlet, through the heater, and to the outlet.

12. The vaporizer device of claim 11, wherein the housing further comprises a second inlet configured to isolate at most a portion of the fluid from the heater.

13. The vaporizer device of claim 12, wherein the first inlet and the second inlet, individually or in combination, have a cross sectional area of at least about 50 mm².

14. The vaporizer device of claim 1, further comprising a valve coupled to an outlet of the reservoir.

15. The vaporizer device of claim 14, wherein at least a portion of the valve is surrounded by the heater, the dispenser, or both.

16. The vaporizer of claim 14, wherein the valve comprises a pressure release valve in a direction from the reservoir to the outlet.

17. The vaporizer device of claim 1, further comprising a preheater configured to heat the medicament in the reservoir, the medicament in the dispenser, or both.

18. The vaporizer device of claim 17, wherein at least a portion of the preheater is at least partially surrounded by the dispenser.

19. The vaporizer device of claim 1, capable of emitting at least about 5 mg/second of the medicament.

20. The vaporizer device of claim 1, capable of forming an aerosol particle of the medicament having a size of greater than about 1 μm.

21. The vaporizer device of claim 1, not comprising a wick.

22. The vaporizer device of claim 1, further comprising an actuator configured to pump the medicament from the reservoir.

23. A vaporizer assembly comprising:
   (a) the vaporizer device of claim 1; and
   (b) a vaporizing base device comprising an actuator configured to pump the medicament from the reservoir.

24. The vaporizer assembly of claim 23, wherein the actuator comprises a motor, a spring, a compressed fluid container, a chemical expander, or any combination thereof.

* * * * *